United States Patent
Asiri et al.

(10) Patent No.: US 11,561,193 B1
(45) Date of Patent: Jan. 24, 2023

(54) SURFACE MODIFIED ELECTRODES, AND METHODS OF PREPARATION THEREOF

(71) Applicant: KING ABDULAZIZ UNIVERSITY, Jeddah (SA)

(72) Inventors: Abdullah Mohamed Asiri, Jeddah (SA); Mohammed Muzibur Rahman, Jeddah (SA); Mohammad Musarraf Hussain, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/827,080

(22) Filed: May 27, 2022

Related U.S. Application Data

(63) Continuation of application No. 17/576,009, filed on Jan. 14, 2022.

(51) Int. Cl.
| | |
|---|---|
| G01N 27/327 | (2006.01) |
| G01N 27/30 | (2006.01) |
| G01N 33/68 | (2006.01) |
| G01N 33/53 | (2006.01) |
| G01N 27/333 | (2006.01) |

(52) U.S. Cl.
CPC ....... *G01N 27/308* (2013.01); *G01N 27/3278* (2013.01); *G01N 27/333* (2013.01); *G01N 33/5308* (2013.01); *G01N 33/6806* (2013.01)

(58) Field of Classification Search
CPC ..... G01N 27/308; G01N 27/327–3278; G01N 27/333; G01N 33/5308
See application file for complete search history.

(56) References Cited

U.S. PATENT DOCUMENTS

| | | | | |
|---|---|---|---|---|
| 6,129,831 | A * | 10/2000 | Temmerman | G01N 27/38 205/780 |
| 2003/0173232 | A1* | 9/2003 | Schulein | G01N 27/308 205/794.5 |
| 2007/0272552 | A1* | 11/2007 | Jiang | E21B 47/10 204/422 |

FOREIGN PATENT DOCUMENTS

WO   WO 2012018777 A1 * 2/2012 ............ B82Y 15/00

OTHER PUBLICATIONS

Goudarzi et al., "Sonochemical synthesis of Tl2O3 nanostructures: supported on multi-walled carbon nanotube modified electrode for monitoring of copper ions," J Mater Scic: Mater. Electron (2016) 27:3675-3682 (Year: 2016).*

(Continued)

*Primary Examiner* — Alexander S Noguerola
(74) *Attorney, Agent, or Firm* — WCF IP

(57) ABSTRACT

A surface modified electrode is provided. The surface modified electrode includes a glassy carbon electrode (GCE) and a nanomaterial disposed on the glassy carbon electrode. The nanomaterial comprises carbon nanotubes (CNTs), and at least one of thallium oxide nanoparticles ($Tl_2O_3$.NPs), thallium oxide ($Tl_2O_3$) nanopowder, and thallium oxide carbon nanotube nanocomposites ($Tl_2O_3$.CNT NCs). A polymer matrix is configured to bind the glassy carbon electrode with the nanomaterial. A method of preparing the surface modified electrode is also disclosed. The surface modified electrode can be implemented in a biosensor for detecting a biological molecule, like choline.

6 Claims, 17 Drawing Sheets

(56) References Cited

OTHER PUBLICATIONS

Yu et al., "A facile and practical biosensor for choline based on manganese dioxide nanoparticles synthesized in-situ at the surface of electrode by one-step electrodeposition," Talanta 146 (2016) 707-713 (Year: 2016).*

Enrico Falcone, Michael Okafor, Nicolas Vitale, Laurent Raibaut, Angélique Sour, et al.. Extracellular Cu2+ pools and their detection : From current knowledge to next-generation probes. Coordination Chemistry Reviews, Elsevier, 2021, 433 (5), pp. 213727. ff10.1016/j.ccr.2020.213727ff. ffhal-03303809 (Year: 2021).*

* cited by examiner

SURFACE MODIFIED ELECTRODES, AND METHODS OF PREPARATION THEREOF

CROSS-REFERENCE TO RELATED APPLICATIONS

This application is a continuation application of U.S. Ser. No. 17/576,009 filed Jan. 14, 2022.

TECHNICAL FIELD

The present disclosure relates to a surface modified electrode, and more specifically, the present disclosure relates to the surface modified electrode for use in a biosensor for detecting a biological molecule.

BACKGROUND

Choline (2-hydroxy-N,N,N-trimethylethanaminium) is a water-soluble ammonium molecule required for different biological functions. It is an important predecessor of the acetylcholine neurotransmitter that is concerned for muscle and memory control. Few important phospholipids, such as phosphatidylcholine, that are responsible for trans-membrane signaling and the structure of the cell membrane, can be synthesized from choline. Primary diagnosis of brain disorders, such as, parkinson's and alzheimer's disease can be analyzed clinically through quantitative assessment of choline. Increased level of choline has been reported to cause an enhanced threat of cancer and DNA damage. Hence, monitoring the choline level is critical in many cases.

Conventional methods for determination of choline, like chemiluminescence, fluorescence, and proton nuclear magnetic resonance suffer from drawbacks such as complexity in operation, long detection times, and high cost. Electrochemical sensors based on enzymatic approach is one of the progressive techniques for the detection of choline in natural science areas such as environmental, industrial, and clinical aspects since it offers rapid, cheap, and simple operation but its dependency on the enzymatic environment makes the application restricted. Owing to such drawbacks, there exists a need to provide a simple, cost-effective, reliable, method for non-enzymatic detection of choline with a short response time.

SUMMARY

The present disclosure relates to a surface modified electrode. The surface modified electrode can be implemented in a biosensor for non-enzymatic detection of biomolecules, particularly choline. The present disclosure also relates to a method of preparing the surface modified electrode.

In one aspect of the present disclosure, the surface modified electrode is disclosed. The surface modified electrode includes a glassy carbon electrode (GCE) and a nanomaterial disposed on the glassy carbon electrode. The nanomaterial includes carbon nanotubes (CNTs), and at least one of thallium oxide nanoparticles ($Tl_2O_3$.NPs), thallium oxide ($Tl_2O_3$) nanopowder and thallium oxide carbon nanotube nanocomposites ($Tl_2O_3$.CNT NCs). In certain embodiments, the carbon nanotube is a single-walled carbon nanotube (SWCNT), a double-walled carbon nanotube (DWCNT), a multi-walled carbon nanotube (MWCNT), or any combination thereof. The surface modified electrode further includes a polymer matrix configured to bind the glassy carbon electrode with the nanomaterial. In some embodiments, the polymer matrix is a sulfonated tetrafluoroethylene-based fluoropolymer (nafion).

The surface modified electrode can be implemented in a biosensor for detecting a biological molecule. In some embodiments, the biological molecule is one selected from a group consisting of acetylcholine, ascorbic acid, cholesterol, choline, dopamine, folic acid, L-glutamic acid, L-glutathione, L-tyrosine, and uric acid. In some embodiments, the biological molecule is choline. In an embodiments, the biosensor is configured to detect choline across a concentration range of 100.0 pM to 100.0 mM. In some embodiments, the biosensor is configured to detect choline having stability for about 30 days. In certain embodiments, the biosensor is configured to detect choline with a detection limit as 9.14 pM, a sensitivity of 104.68 $\mu A \mu M^{-1} cm^{-2}$, a linear dynamic range in the range of 100.0 pM-1.0 mM, and a linearity value in the linear dynamic range as 0.9884.

In another aspect of the present disclosure, a method of preparing the surface modified electrode is described. The method includes mixing carbon nanotubes (CNT's), and at least one of thallium oxide nanoparticles ($Tl_2O_3$.NPs), thallium oxide ($Tl_2O_3$) nanopowder, and thallium oxide carbon nanotube nanocomposites ($Tl_2O_3$.CNT NCs), in an organic solvent to form a slurry of the nanomaterial. The method also includes disposing the slurry of the nanomaterial on the glassy carbon electrode to form a film. In certain embodiments, the slurry of the nanomaterial is disposed on the glassy carbon electrode for a period of 1-3 hours at a temperature range of 35-40° C. Further, a polymer matrix is coated on the film to obtain the surface modified electrode. In some embodiments, the polymer matrix is coated on the film for a period of 2-4 hours at a temperature range of 35-40° C. The polymer matrix is a sulfonated tetrafluoroethylene-based fluoropolymer (nafion).

In some embodiments, the method further includes obtaining the thallium oxide carbon nanotube nanocomposites ($Tl_2O_3$.CNT NCs) by stirring a salt of thallium in water in an alkaline medium to form a first mixture. In some embodiments, the salt of thallium is stirred in water in an alkaline medium for a period of 5-7 hours at a temperature range of 80° C.-100° C. In an example, the salt of thallium is thallium nitrate $Tl(NO_3)_3$. The method further includes washing the first mixture to obtain a second mixture, and drying the second mixture to obtain the thallium oxide carbon nanotube nanocomposites. In certain embodiments, the second mixture was dried for a period of 10-14 hours at a temperature range of 25-37° C.

The foregoing as well as other features and advantages of the present disclosure will be more fully understood from the following description, examples, and claims.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
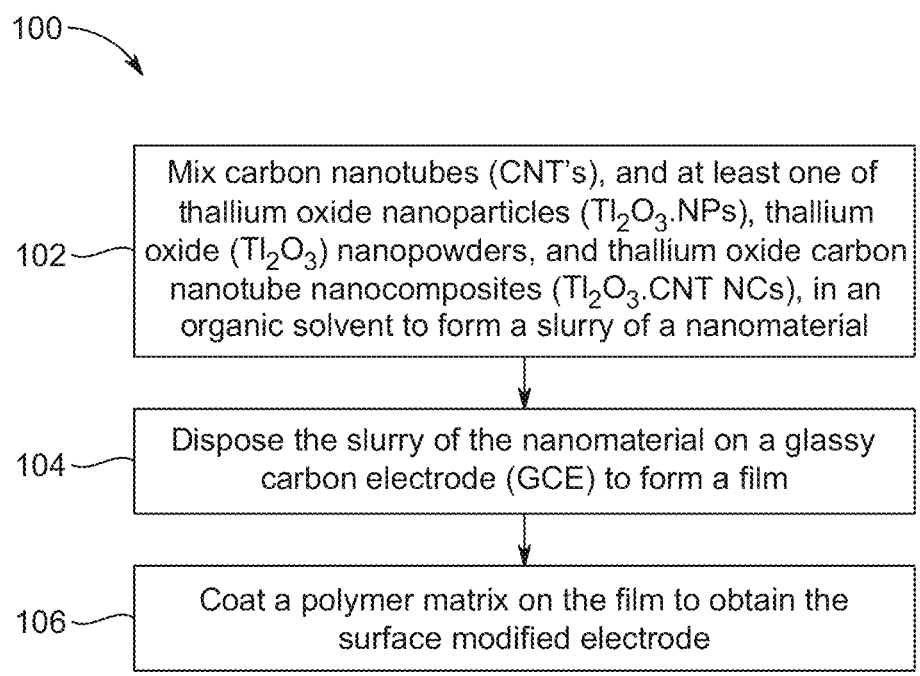
FIG. 1 is an exemplary flowchart illustrating a method for preparing the surface modified electrode.

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements. A skilled artisan will appreciate that various alternate embodiments and forms may be prepared. Examples, therefore, given are only for illustration purposes without any intention to restrict the embodiments to a given set of examples. Specific functional aspects are provided merely to enable a person skilled in the art to perform the invention and should not be construed as limitations of the invention. Any method steps and processes described herein are not to be construed as necessarily requiring their performance in the particular order discussed or illustrated, unless specifically identified as an order of performance. It is also to be understood that additional or alternative steps may be employed, unless otherwise indicated.

As used herein, "surface modified electrode" refers to an electrode treated to modify the surface properties, and enhance electrochemical functions.

As used herein, "nanomaterial" refers to chemical substances or materials having particle sizes between 1 to 100 nanometers in at least one dimension.

As used herein, "carbon nanotubes (CNTs)" refers to a single-walled carbon nanotube (SWCNT), a double-walled carbon nanotube (DWCNT), a multi-walled carbon nanotube (MWCNT).

The term "glassy carbon" refers herein to a non-graphitizing carbon which combines glassy and ceramic properties with those of graphite.

As used herein, "mixing" refers to combining two or more materials together with the use of a mixer or any other device.

As used herein, "working electrode" refers to the electrode in an electrochemical cell/device/biosensor on which the electrochemical reaction of interest is occurring.

As used herein, "counter-electrode", is an electrode used in an electrochemical cell for voltametric analysis or other reactions in which an electric current is expected to flow.

As used herein, "limit of detection (LOD)" is the smallest concentration of an analyte in a test sample that can be easily distinguished from zero.

As used herein, "limit of quantification (LoQ)" is the smallest concentration of an analyte in the test sample that can be determined with acceptable repeatability and accuracy.

As used herein, "linear dynamic range (LDR)" is the range of concentrations where the signals are directly proportional to the concentration of the analyte in the sample.

As used herein, "selectivity" is the quality of the electrochemical response that can be achieved without interference for any other substance.

As used herein, "sensitivity" is the change in the electrochemical response with regard to a change in the concentration of the analyte.

As used herein, a "voltammogram" is a graph that can be drawn after an electrochemical experiment. This graph has a typical, recognizable form in which the electron flow (current: I) is measured in Volt against the potential (E).

As used herein, "amount" refers to the level or concentration of one or more elements or end-products of the system and the methods of the present disclosure.

The use of the singular herein includes the plural (and vice versa) unless specifically stated otherwise.

The use of the terms "include," "includes", "including," "have," "has," or "having," "comprise," "comprises," "comprising" or the like should be generally understood as open-ended and non-limiting unless specifically stated otherwise.

It is understood that the order of steps or order for performing certain actions can be changed so long as the intended result is obtained. Moreover, two or more steps or actions may be conducted simultaneously.

As used herein, the term "about" or "between" refers to a ±20% to ±10% variation from the nominal value unless otherwise indicated.

Embodiments of the present disclosure are directed towards a surface modified electrode. The surface modified electrode consists of a glassy carbon electrode (GCE) modified/fabricated with carbon nanotube thallium oxide based nanomaterial. The surface modified electrode when implemented in a biosensor functions as a working electrode, and is effective in detection of biomolecules with high selectivity, sensitivity, across a wide concentration range, with a short response time. In an example, the biomolecule is choline. The electrochemical characteristics of the surface modified electrode were found to be much superior in comparison to the bare electrode or the glassy carbon electrode, confirming the superiority of the carbon nanotube thallium oxide based nanomaterial disposed on the biosensor. Although, the present disclosure describes the use of the biosensor for detection of choline in a non-enzymatic environment, the sensor of the present disclosure may be adapted for detection of other biomolecules as well.

In an embodiment, the surface modified electrode includes a glassy carbon electrode modified/fabricated with a nanomaterial disposed on at least a portion of the glassy carbon electrode. In an example, the nanomaterial may be disposed across the length of the glassy carbon electrode with a uniform thickness or may be disposed on portions of the glassy carbon electrode. The fabrication of the nanomaterial over the glassy carbon electrode may be done by any conventional methods known in the art. In an example, the fabrication is done by drop casting technique. The nanomaterial includes carbon nanotubes (CNT's) in addition to one or more of thallium oxide nanoparticles ($Tl_2O_3$.NPs), thallium oxide ($Tl_2O_3$) nanopowder and thallium oxide carbon nanotube nanocomposites ($Tl_2O_3$.CNT NCs). In an embodiment, the glassy carbon electrode is disposed with CNT's, $Tl_2O_3$.NPs, $Tl_2O_3$ nanopowders, and $Tl_2O_3$.CNT NCs. In another embodiment, the glassy carbon electrode is disposed with CNT's, $Tl_2O_3$.NPs and $Tl_2O_3$.CNT NCs. The carbon nanotube may be a single-walled carbon nanotube (SWCNT), a double-walled carbon nanotube (DWCNT), a multi-walled carbon nanotube (MWCNT), or any combination thereof.

The surface modification of the glassy carbon electrode with the carbon nanotubes and the nanomaterial is to impart desirable physical and chemical properties, such as increased surface area, or adsorption or absorption capacity to biomolecules of interest. In an example, thickness of the nanomaterial disposed on the glassy carbon electrode is about 10 nanometer to about 50 nanometer. The surface modified electrode further includes a polymer matrix that is configured to bind the glassy carbon electrode with the nanomaterial by a chemical bond. In an example, the nature of bonding between the nanomaterial and the glassy carbon electrode, facilitated through the polymer matrix, is a covalent bond. In another example, the nature of bonding between the nanomaterial and the glassy carbon electrode is physical adsorption. In some embodiments, the polymer matrix may be a sulfonated tetrafluoroethylene-based fluoropolymer (nafion or NFN). The surface modified electrode is GCE/$Tl_2O_3$.CNT NCs/NFN The present disclosure also describes a biosensor for detecting the biological molecule. The biosensor is a two-electrode system having the surface modified electrode as a working electrode, and a platinum wire as a counter-electrode. The working electrode and the counter-electrode may be connected to each other by way of electrical interconnects that allow for passage of current between the electrodes, when a potential is applied between them. The working electrode and the counter-electrode may be arranged as obvious to a person of ordinary skill in the art. In an example, the electrode configuration of the electrochemical sensor may be designed based on the type of the biomolecule to be detected and type of detection methodology. Although the present disclosure describes a two-electrode system (the working electrode and the counter-electrode) in the sensor, the sensor may be adapted to have a 3-electrode or a 4-electrode or a multi-electrode system to detect one or more biomolecules of interest. In certain embodiments, the working electrode has a cross-section diameter of 1.68 millimeters, and the counter-electrode as a cross-section diameter of 0.2 millimeters. In certain other embodiments, the working electrode and the counter-electrode can have same dimensions.

The biosensor having the surface modified electrode can be used to detect one or more biological molecules. In certain embodiments, the biological molecule may be one selected from a group consisting of acetylcholine, ascorbic acid, cholesterol, choline, dopamine, folic acid, L-glutamic acid, L-glutathione, L-tyrosine, and uric acid. In one embodiment, the biological molecule is choline. Although embodiments of the present disclosure are directed towards detection of choline, it may be understood by a person of ordinary skill in the art that the biosensor may be adapted for detection of other biological molecules as well.

The sensor becomes operable when the biomolecule of interest, such as choline is brought in contact with the working electrode. A chemical reaction between the working electrode and the biological molecule occurs causing a change in chemical information associated with the biological molecule. In an example, the change in chemical information could be a change in oxidation state. In other words, the biological molecule may undergo a redox (oxidation-reduction) reaction resulting in loss of electrons, when it is brought in contact with the working electrode. The sensor is configured to determine a change in chemical information caused by the biological molecule on contact with at least a portion of the surface modified electrode, and further transduce the change in chemical information associated with the biological molecule to an electrical signal. In certain embodiments, the electrical signal is indicative of a concentration level of the biological molecule. Therefore, the greater the concentration of the biological molecule, the stronger is the signal.

In some embodiments, the biosensor may be configured to detect choline across a concentration range of 100.0 pM~100.0 mM.

In another embodiment, the biosensor may be configured to detect choline having stability for up to about 30 days.

In yet another embodiment, the biosensor configured to detect choline has a detection limit of sensor as 9.14 pM.

In another embodiment, the biosensor configured to detect choline has a sensitivity of 104.68 $\mu A \mu M^{-1} cm^{-2}$.

In another embodiment, the biosensor configured to detect choline has a the linear dynamic range as 100.0 pM-1.0 mM.

In yet another embodiment, the biosensor configured to detect choline has a linearity value in the linear dynamic range as 0.9884.

Referring to FIG. 1A, a method for preparing the surface modified electrode is described. In an embodiment, the method 100 includes mixing carbon nanotubes (CNT's), and at least one of thallium oxide nanoparticles ($Tl_2O_3$.NPs), thallium oxide ($Tl_2O_3$) nanopowders, and thallium oxide carbon nanotube nanocomposites ($Tl_2O_3$.CNT NCs), in an organic solvent to form a slurry of the nanomaterial (102). In an embodiment, the CNT's, $Tl_2O_3$.NPs, $Tl_2O_3$ nanopowders, and $Tl_2O_3$.CNT NCs are mixed in an organic solvent to form a slurry of the nanomaterial. In another embodiment, the CNT's, $Tl_2O_3$.NPs and $Tl_2O_3$.CNT NCs are mixed in an organic solvent to form a slurry of the nanomaterial. The carbon nanotube may be a single-walled carbon nanotube (SWCNT), a double-walled carbon nanotube (DWCNT), a multi-walled carbon nanotube (MWCNT), or any combination thereof. The organic solvent is a lower alcohol, such as ethanol. The method further includes deposing the slurry of the nanomaterial on the glassy carbon electrode to form a film. In certain embodiments, the method includes disposing the slurry of the nanomaterial with the glassy carbon electrode for a period of 1-3 hours at a temperature range of 35-40° C. (104). The method also includes coating the polymer matrix on the film to obtain the surface modified electrode (106). In one embodiment, the method includes coating the polymer matrix on the film for a period of 2-4 hours at a temperature range of 35-40° C. In another embodiment, the polymer matrix is a sulfonated tetrafluoroethylene-based fluoropolymer (Nafion). In certain embodiments, the polymer matrix may be added to the glassy carbon electrode in a drop-wise manner and kept open in the air so as to synchronize coating development.

In some embodiments, a method for preparing the thallium oxide nanocomposites ($Tl_2O_3$.CNT NCs) is described. The method includes stirring a salt of thallium in water in an alkaline medium to form a first mixture. The salt of thallium may be thallium nitrate $Tl(NO_3)_3$. In one embodiment, the method includes stirring the salt of thallium in water in an alkaline medium for a period of 3-8 hours at a temperature range of about 70° C.-110° C. In another embodiment, the method includes stirring the salt of thallium in water in an alkaline medium for a period of 5-7 hours at a temperature range of about 80° C.-100° C. In yet another embodiment, the method includes stirring the salt of thallium in water in an alkaline medium for a period of 4 hours at 90° C. In certain embodiments, the alkaline medium of the first mixture may be obtained by the addition of a base component such as, but not limited to, NaOH, KOH, $Ca(OH)_2$, or a combination thereof. In some embodiments, the stirring may be done by equipment such as, but not limited to, magnetic stirrer, stirring motors, shakers, and small pumps, etc. The method further includes washing the first mixture to obtain a second mixture. In certain embodiments, the first mixture may be washed with water and acetone and kept in the open air for 1.5 hours at room temperature. The method also includes drying the second mixture to obtain the thallium oxide nanocomposites. In one embodiment, the method may include drying the second mixture for a period of 8-16 hours at a temperature range of about 22° C.-40° C. In another embodiment, the method may include drying the second mixture for a period of 10-14 hours at a temperature range of about 25° C.-37° C. In yet another embodiment, the method may include drying the second mixture for a period of 12 hours at a temperature range of about 28° C.-34° C. In certain embodiments, the drying of the second mixture may be accomplished by putting the second mixture in an oven for about 24 hours at 60° C.

The surface modified electrode used in the biosensor allows for ultrasensitive detection of biological choline in a non-enzymatic environment with higher selectivity, sensitivity, good reliability with a short response time.

EXAMPLES

The disclosure will now be illustrated with examples, which is intended to illustrate the working of disclosure and not intended to take restrictively to imply any limitations on the scope of the present disclosure.

Example 1: Process of Preparation of Thallium Oxide Carbon Nanotubes Carbon Nanocomposites ($Tl_2O_3$.CNT NCs)

$Tl(NO_3)_3$, CNT, and NaOH are used as reacting agents in the preparation of $Tl_2O_3$.CNT NCs by using a simple wet-chemical procedure (WCP) [M. M. Hussain, M. M. Rahman, A. M. Asiri. M. R. Awual. RSC, Non-enzymatic simultaneous detection of Lglutamic acid and uric acid using mesoporous $Co_3O_4$ nanosheets, Adv. 6 (2016) 80511-80521, M. M. Hussain, M. M. Rahman, A. M. Asiri. J. Environ, Ultrasensitive and selective 4-aminophenol chemical sensor development based on nickel oxide nanoparticles decorated carbon nanotube nanocomposites for green environment, Sci. 53 (2017) 27-38]. WCP is an established solid-state method, generally used in the preparation of un-doped or doped nanocomposites. According to this procedure, $Tl(NO_3)_3$ was dissolved under non-stop stirring with distilled water (100.0 mL) in a conical flask (250.0 mL) and the pH of the resultant solution was maintained above 10.0 by addition of NaOH. After 6.0 hours of constant stirring on a hot plate at 90.0° C., the flask was washed methodically with distilled water and acetone, and kept for drying in the open air for about 12 hours at room temperature to obtain the $Tl_2O_3$.CNT NCs. Thallium oxide nanoparticles ($Tl_2O_3$ NPs) were also prepared in the same way. The prepared slurry of $Tl_2O_3$ NPs and $Tl_2O_3$.CNT NCs were dried in the oven at a temperature of 60.0° C. for 24.0 h, followed by grinding into particles and powders. The particles and powders were dried again in the oven at a temperature of 60.0° C. for 24.0 hours for use in electrochemical experimentation and applications. A possible mechanism regarding the preparation of $Tl_2O_3$.CNT NCs is presented in the following equations(i)-(iv)}.

$$NaOH \rightarrow Na^+ + OH^- \qquad (i)$$

$$Tl(NO_3)_3 \rightarrow Tl^{3+} + 3NO_3^- \qquad (ii)$$

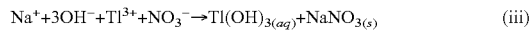
$$Na^+ + 3OH^- + Tl^{3+} + NO_3^- \rightarrow Tl(OH)_{3(aq)} + NaNO_{3(s)} \qquad (iii)$$

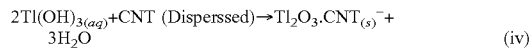
$$2Tl(OH)_{3(aq)} + CNT\ (Disperssed) \rightarrow Tl_2O_3.CNT_{(s)} + 3H_2O \qquad (iv)$$

Example 2: Preparation of Glassy Carbon Electrode (GCE) with the $Tl_2O_3$.CNT NCs According to the procedures mentioned by M. M. Hussain and his co-workers, the required amounts of the glassy carbon electrode (GCE) were prepared and modified as provided in the literature N. M. Hussain, M. M. Rahman, M. N. Arshad, A. M. Asiri., Trivalent Y3+ ionic sensor development based on (E)-Methyl-N'-nitrobenzylidene-benzenesulfonohydrazide (MNBBSH) derivatives modified with nafion matrix, Sci. Rep. 7 (2017) 5832, M. M. Hussain, M. M. Rahman, M. N. Arshad, A. M. Asiri., Electrochemical Detection of Ni2+ Ions Using Synthesized (E)-N'-Chlorobenzylidene-4-methylbenzenesulfonohydrazide Derivatives Modified with a Nafion Matrix, ChemistrySelect 2 (2017) 7455-7464, M. M. Hussain, A. M. Asiri, M. N. Arshad, M. M., Synthesis, characterization, and crystal structure of (E)-N'-(4-Bromobenzylidene)-benzenesulfonohydrazide and its application as a sensor of chromium ion detection from environmental samples, Rahman J Molecular Structure 1207 (2020) 127810]. A phosphate buffer adapted to a range of pH values, from light acidic to basic phases such as pH=5.7, 6.5, 7.0, 7.5, and 8.0, was prepared by dissolving $NaH_2PO_4$ in distilled water. Further, the GCE is washed with distilled water and then acetone systematically and was positioned to dry in the open air for about 1.30 hours. $Tl_2O_3$ NPs, $Tl_2O_3$.CNT NCs and CNT were mixed with ethanol (EtOH) to prepare a slurry. The slurry was applied on the dried upper surface of the GCE. The GCE was further covered, and was placed in the open air to dry for about 1.30 hours. Polymer conducting matrix such as nafion (NFN) was added to the covered GCE in a dropwise manner and kept in an open environment for about 2.0 hours so as to synchronize the coating development. Platinum wire was used as a counter-electrode, and the surface modified GCE was used as a working electrode to document the electrical responses associated with identification and detection of the biological molecule.

Materials and Methods

Thallium nitrate $[Tl(NO_3)_3]$, carbon nanotubes (CNT), acetylcholine, ascorbic acid, cholesterol, choline, dopamine, folic acid, L-glutamic acid, L-glutathione, L-tyrosine, and uric acid, ethanol, nafion, and NaOH were received from the Sigma-Aldrich company (KSA). UV-Visible and Fourier transform-infrared (FTIR) spectra of the prepared $Tl_2O_3$ NPs and $Tl_2O_3$.CNT NCs were recorded respectively on a Thermo scientific 300 k UV-Visible spectrophotometer and NICOLET iS50 FTIR spectrometer (Madison, USA). X-ray diffraction (XRD) experimentation was performed under ambient environment to determine the crystalline nature of $Tl_2O_3$ NPs and $Tl_2O_3$.CNT NCs. Field emission scanning electron microscope (FESEM) (JSM-7600F, JEOL, and Japan) attached with energy-dispersive X-ray spectroscopy (EDS) was used to analyse the electrochemical criteria (arrangement, elemental analysis, morphology, and particle size) of the $Tl_2O_3$ NPs and $Tl_2O_3$.CNT NCs had been recorded. Binding energy between Cu and O was determined by means of X-ray photoelectron spectroscopy (XPS) experimentation on a thermo scientific A1 K-α1 1066 spectrometer having an excitation radiation resource (Beam spot size=300.0 μm, pressure=$10^{-8}$ torr, and pass energy=200.0 eV). Current-voltage experimentation was performed based on an electrometer (Keithley, USA) at a selective point in order to measure desired sensitive and selective biological molecule by using the sensor of the present disclosure ($Tl_2O_3$.CNT NCs/GCE/NFN).

Results and Discussion

Examination of Optical Characteristics

Figure 2A:
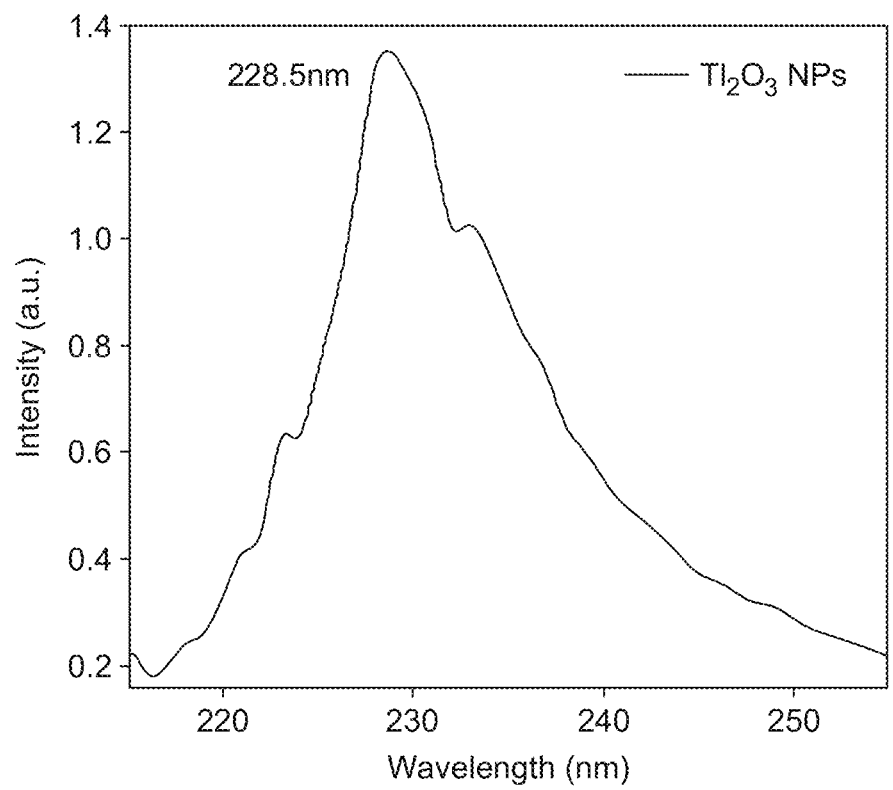
FIG. 2A shows a ultraviolet (UV) spectrum of thallium oxide ($Tl_2O_3$) nanoparticles.
Figure 2B:
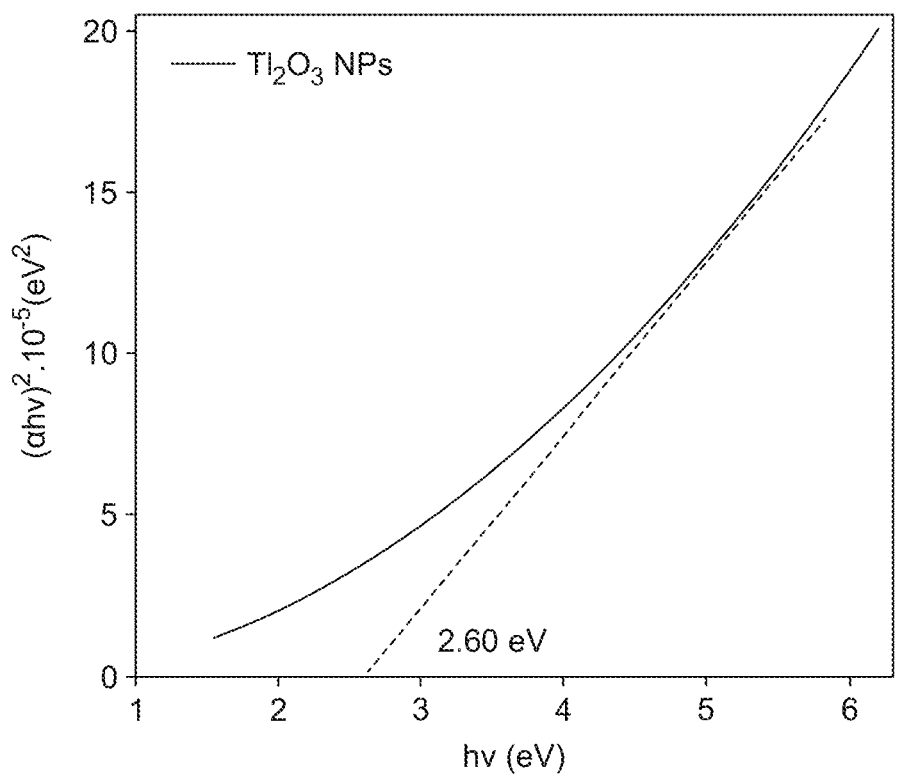
FIG. 2B is a bandgap energy plot of $Tl_2O_3$ NPs.
Figure 2C:
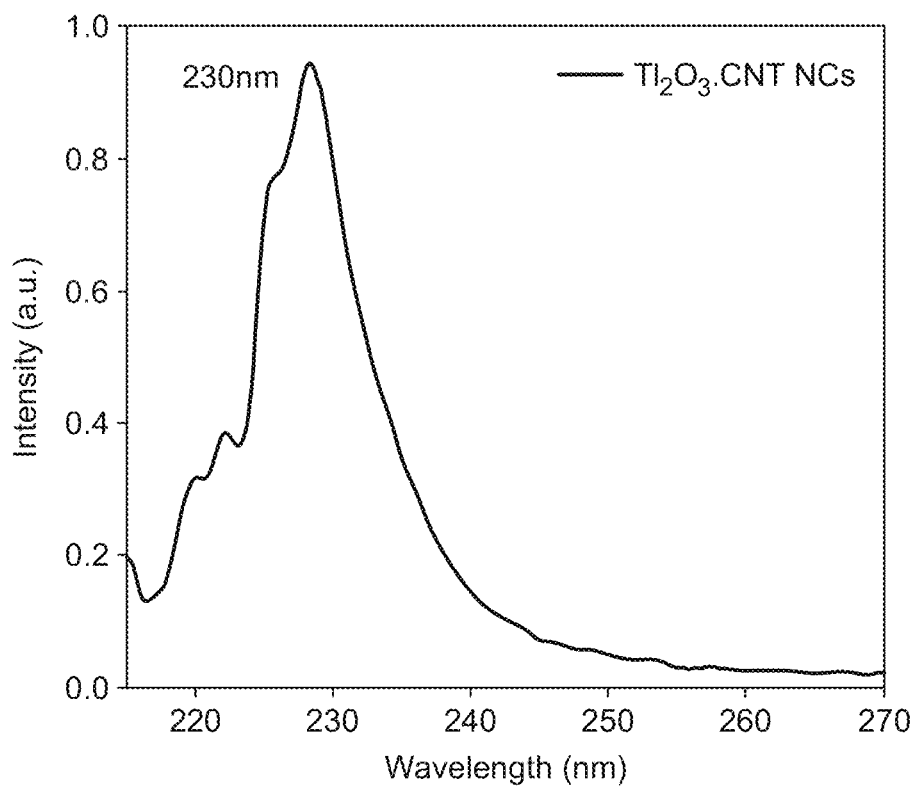
FIG. 2C shows the UV spectrum of thallium oxide carbon nanotube nanocomposites ($Tl_2O_3$.CNT NCs)
Figure 2D:
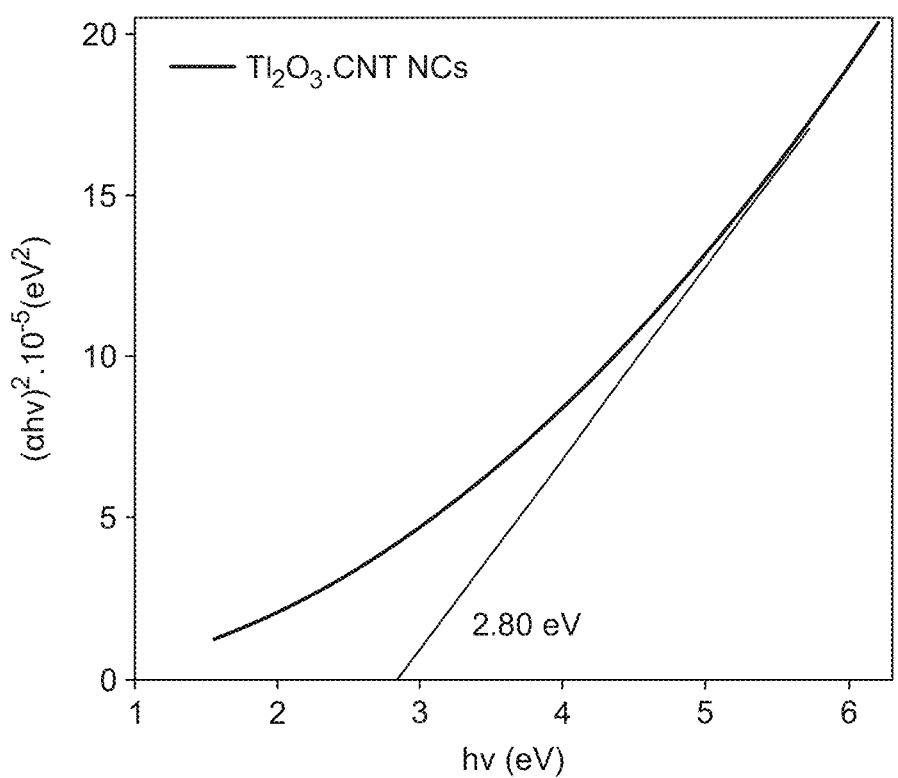
FIG. 2D is the bandgap energy plot of the $Tl_2O_3$.CNT NCs.

FIG. 2A and FIG. 2B shows UV examination results and bandgap energies examination results of $Tl_2O_3$ NPs. Bandgap energy and spectra of the thallium oxide may be achieved based on the UV-Visible spectroscopy principle due to the adsorption of radiant force throughout the movement of the external electrons of the atom to the higher energy phase. FIG. 2C and FIG. 2D shows UV examination results and bandgap energies examination results of $Tl_2O_3$.CNT NCs. Wide-ranging absorption UV-visible curves of $Tl_2O_3$ NPs and $Tl_2O_3$.CNT NCs were achieved at 228.5 nm and 230.0 nm which was recorded in the range of 200-800 nm (as shown in FIG. 2A and FIG. 2C). Based on the direct bandgap rule (Tauc's equation, v), theoretical band gap energies (BGE) of the $Tl_2O_3$ NPs (5.43 eV) and $Tl_2O_3$.CNT NCs (5.39) was achieved. After that hv vs (αhv)2 are plotted and extended to the x-axis (Equations vi-viii) to determine practical BGE of the $Tl_2O_3$ NPs (2.60 eV) and $Tl_2O_3$.CNT NCs (2.80 eV) (as shown in FIG. 2B and FIG. 2D). Here, A=constant related to the effective mass of the electrons, h=Plank's constant, v=Frequency, α=absorption coefficient, and r=0.5.

Figure 3A:
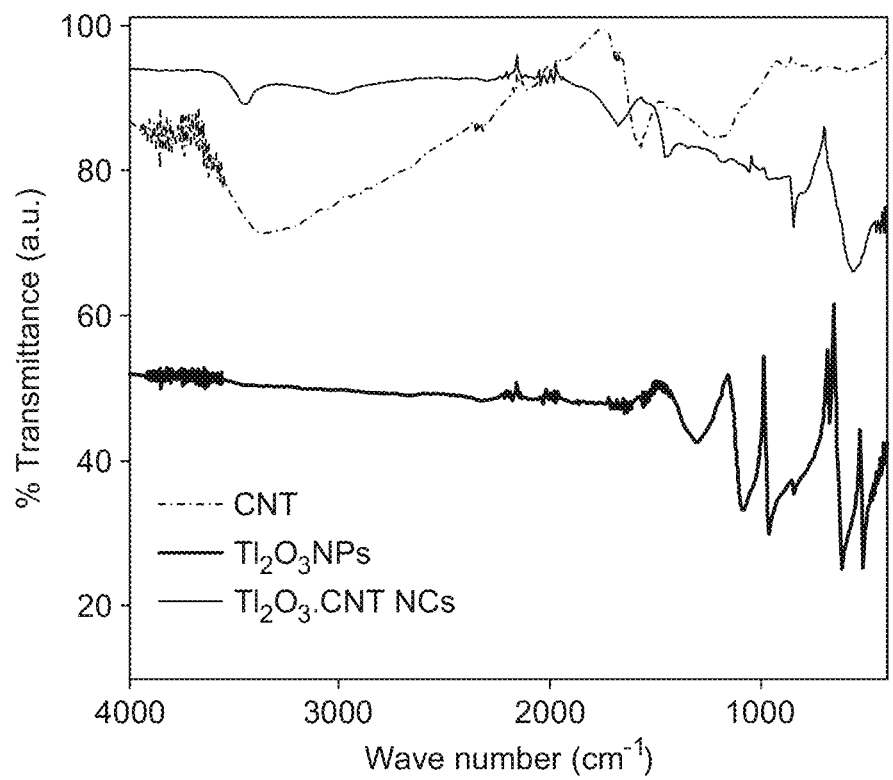
FIG. 3A shows a fourier-transfer infrared spectroscopy (FT-IR) spectrum of carbon nanotubes (CNT), thallium oxide ($Tl_2O_3$) nanoparticles, and thallium oxide carbon nanotube nanocomposites ($Tl_2O_3$.CNT NCs)

FIG. 3A shows Fourier transfer infrared spectroscopy (FTIR) studies of CNT, $Tl_2O_3$ NPs, and $Tl_2O_3$.CNT NCs. FT-IR assessment was performed in the region of 4000-400 $cm^{-1}$ under a standard environment to recognize the functional character of the $Tl_2O_3$ NPs and $Tl_2O_3$.CNT NCs. Reported peaks in 1806, 1315, 1095, 977, and 610 $cm^{-1}$ were assigned to the presence of —C≡C—, —C═C—, C—H, ═Tl—O—Tl═, and —Tl═O in the nanocomposite (As shown in FIG. 3A). The assigned peaks at 1095 $cm^{-1}$ and 610 $cm^{-1}$ signified the understanding of the metal-oxide bond (—Tl═O) confirming the formation of the $Tl_2O_3$.CNT NCs.

Figure 3B:
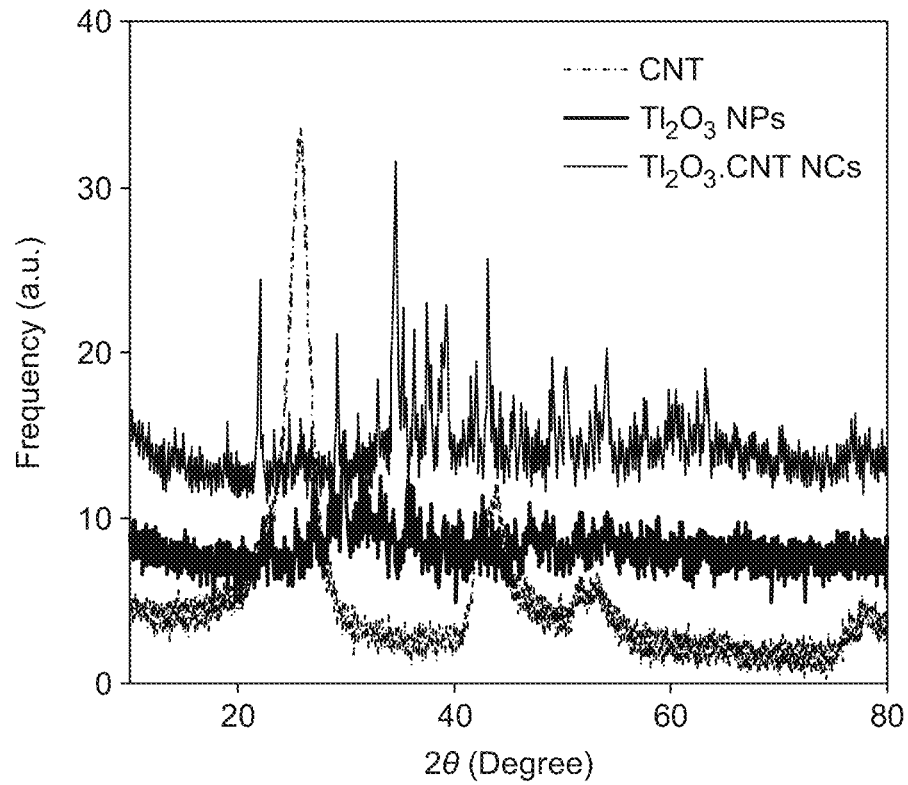
FIG. 3B shows X-ray diffraction (XRD) studies of CNTs, $Tl_2O_3$ nanoparticles, and $Tl_2O_3$.CNT NCs.

FIG. 3B shows X-Ray Diffraction (XRD) studies of CNT, $Tl_2O_3$ NPs, and $Tl_2O_3$.CNT NCs. XRD examination was conducted in the range of 2θ=10°-80° to understand the crystalline nature of the $Tl_2O_3$.CNT NCs. Impending peaks intensity with signal for 2θ were obtained at 211°, 222°, 400°, 431°, 440°, 611°, and 541°, in accordance with the literature values. These potential peaks are an indication of the crystalline nature and purity of the nanocomposites. According to the XRD examination, it can be observed that a good number of crystalline $Tl_2O_3$.CNT was present in the prepared $Tl_2O_3$.CNT NCs. By using the Scherer formula (ix), the crystallite size of the prepared $Tl_2O_3$ NPs and $Tl_2O_3$.CNT NCs were found as 341.32 nm and 34.34 nm respectively.

Figure 4A:
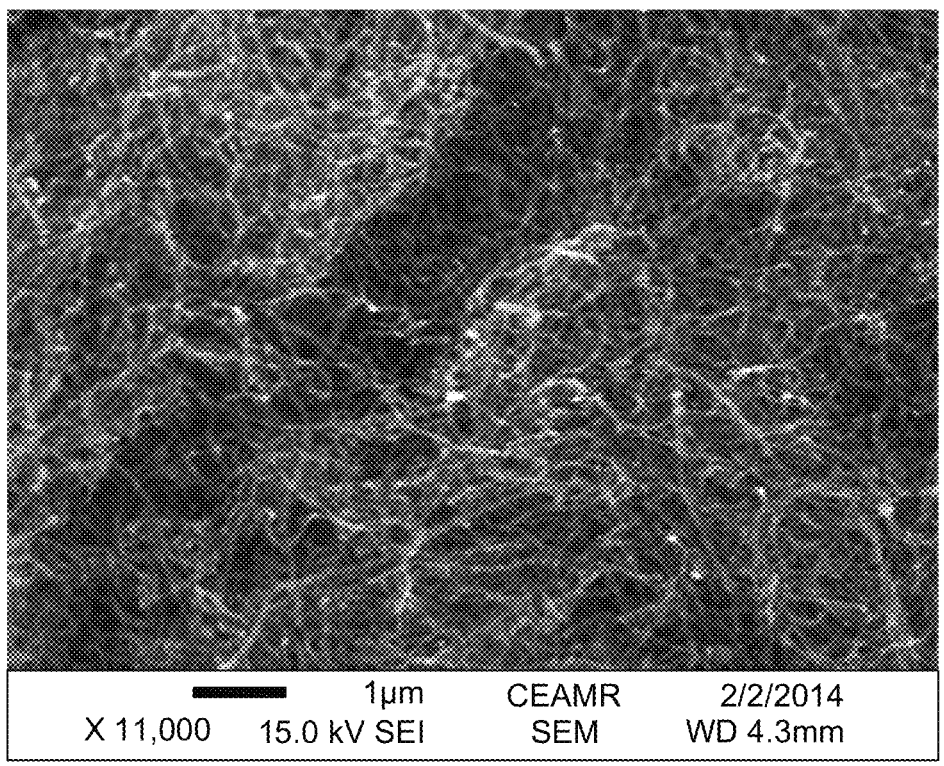
FIG. 4A shows Field Emission Scanning Electron Microscope (FESEM) image of CNT.
Figure 4B:
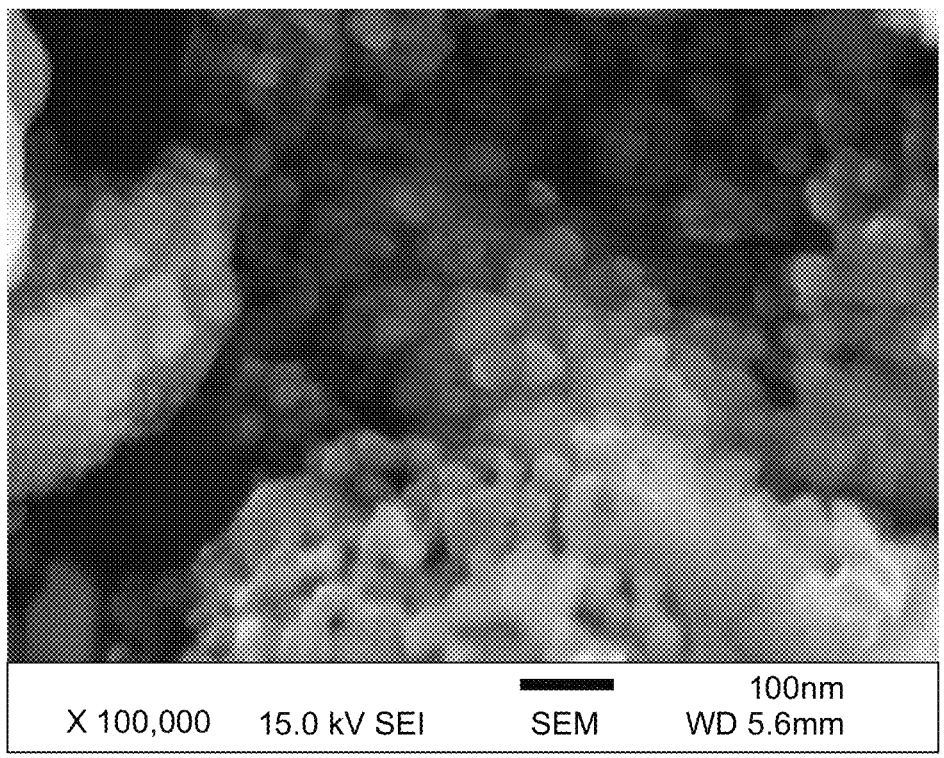
FIG. 4B shows FESEM image of $Tl_2O_3$ NPs.
Figure 4C:
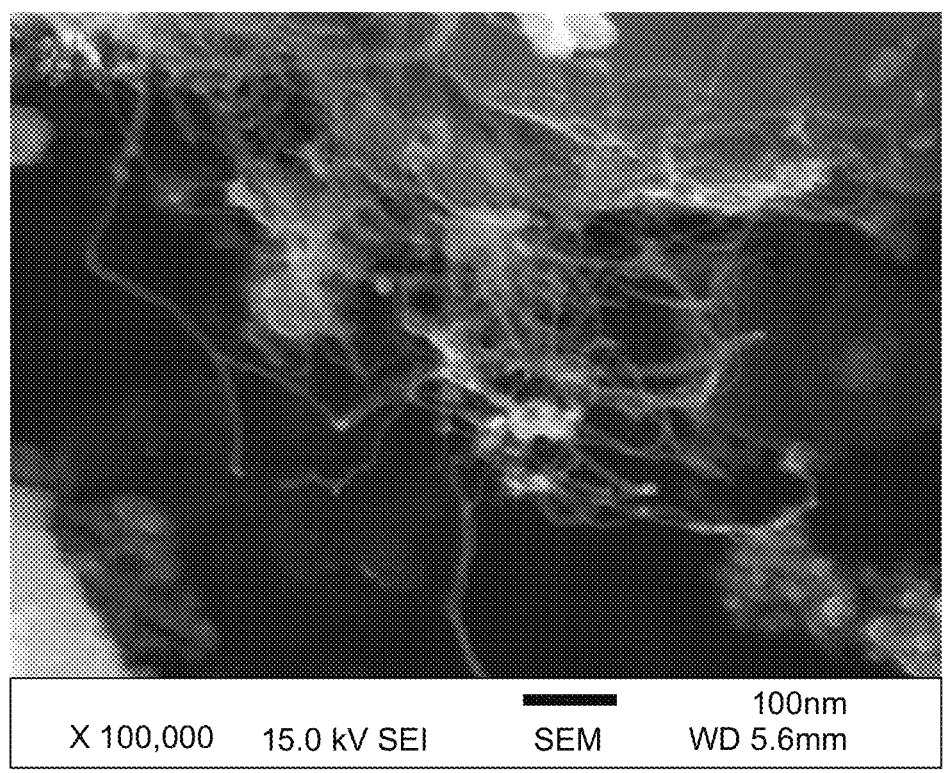
FIG. 4C shows FESEM image of $Tl_2O_3$.CNT NCs.
Figure 4D:
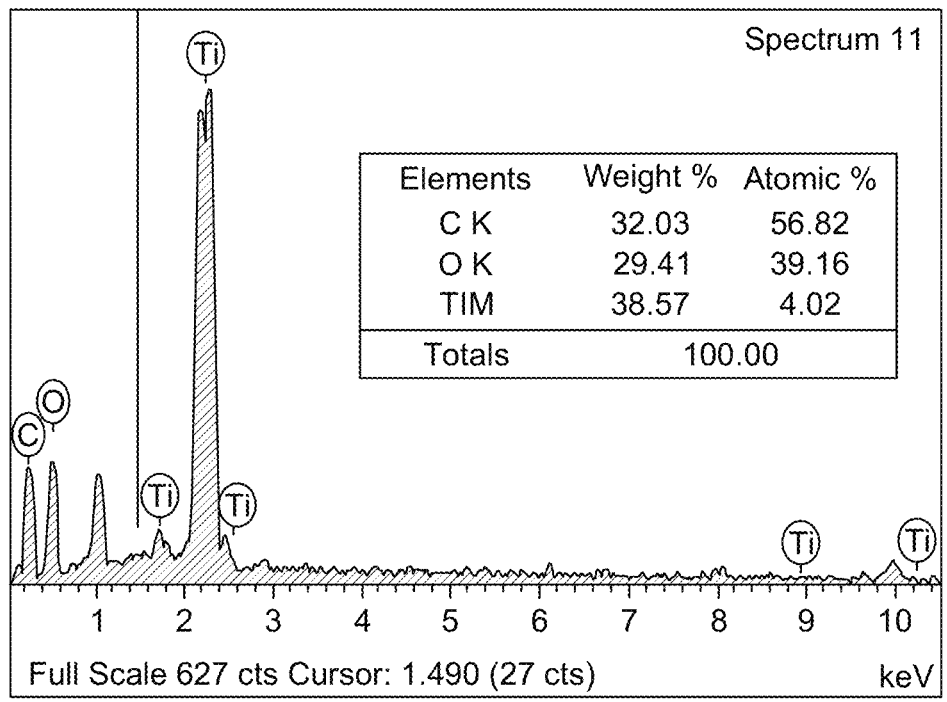
FIG. 4D shows elemental analysis of $Tl_2O_3$.CNT NCs.

Referring to FIG. 4A, FIG. 4B, and FIG. 4C, shows field emission scanning electron microscope (FESEM) images of CNT, $Tl_2O_3$ NPs, and $Tl_2O_3$.CNT NCs. FESEM was used to examine the morphological properties of $Tl_2O_3$.CNT NCs. Elemental characteristics of the arranged $Tl_2O_3$.CNT NCs were examined using FESEM equipped with X-ray energy dispersive spectroscopy (XEDS). Characteristic FESEM images of the CNT, $Tl_2O_3$ NPs, and $Tl_2O_3$.CNT NCs were recorded from low to high exaggerated range (diameter of $Tl_2O_3$.CNT was found to be in the range of 8.0 nanometers to 15.0 nanometers, specifically 10.0 nanometers). FIG. 3D shows elemental analysis of $Tl_2O_3$.CNT NCs. Based on the XEDS experimentation, it was observed that carbon (C), thallium (Tl), and oxygen (O) were found in the prepared $Tl_2O_3$.CNT NCs. These nanocomposites consist of carbon (32.03%), oxygen (29.41%), and thallium (38.57%) in weight. No additional peaks suggesting impurities were observed in the analysis, confirming that that the nanocomposites formed were only composed of carbon, thallium, and oxygen.

Figure 5A:
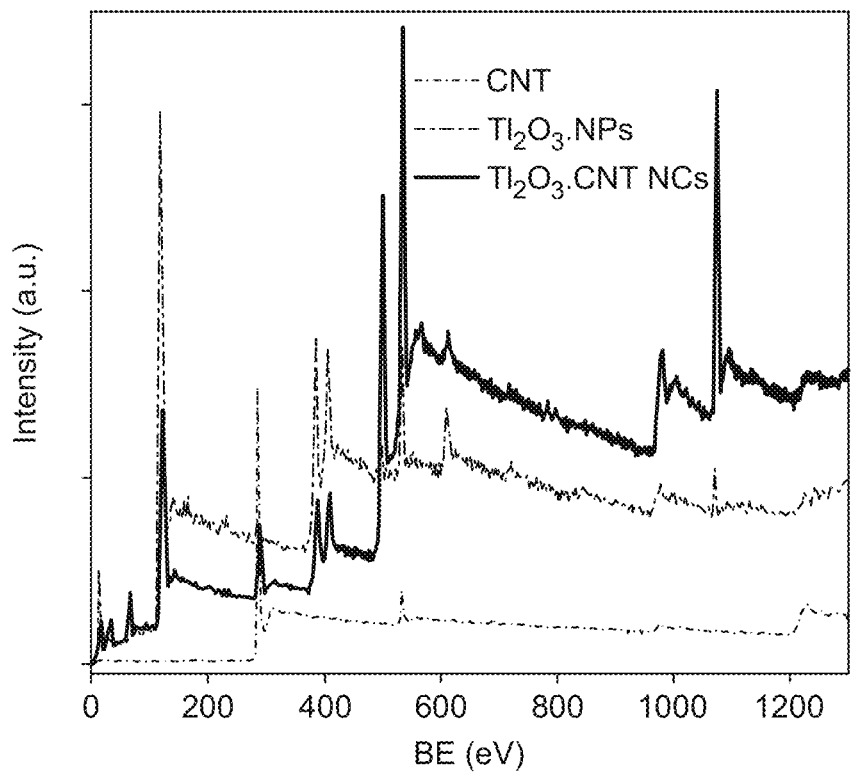
FIG. 5A shows comparative binding energy examination of CNT, $Tl_2O_3$ NPs, $Tl_2O_3$.CNT NCs.
Figure 5B:
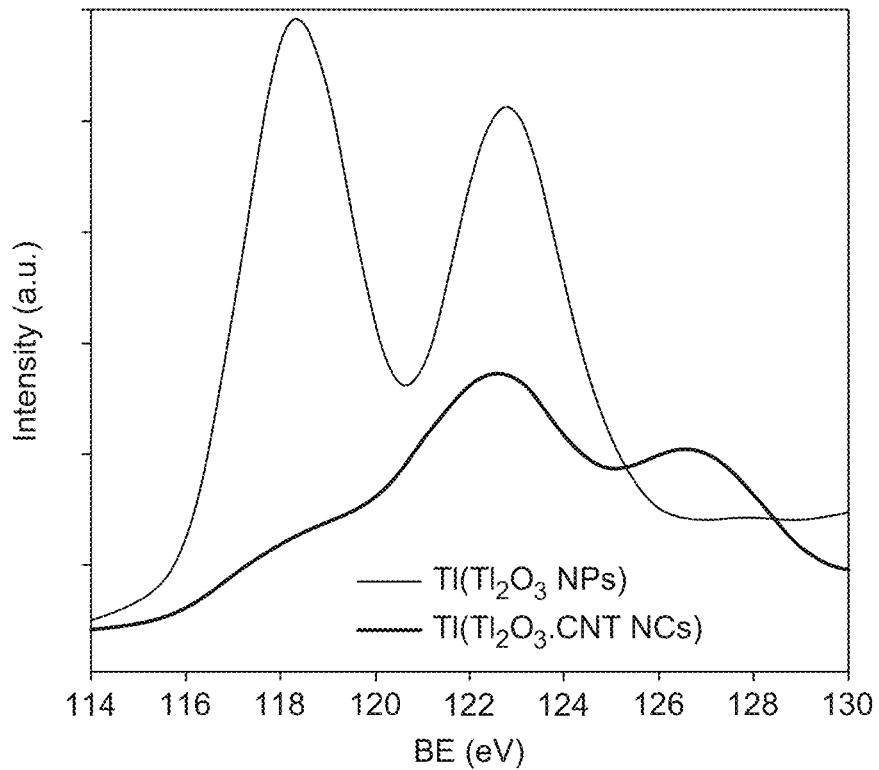
FIG. 5B shows binding energy examination of $Tl^{3+}$.
Figure 5C:
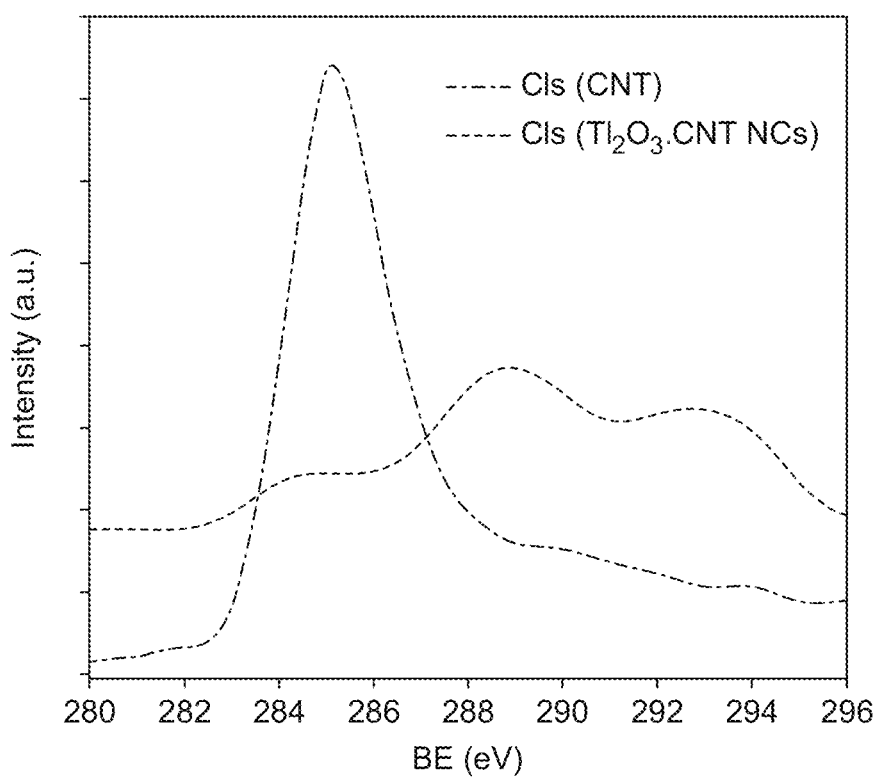
FIG. 5C shows binding energy examination of C1s.
Figure 5D:
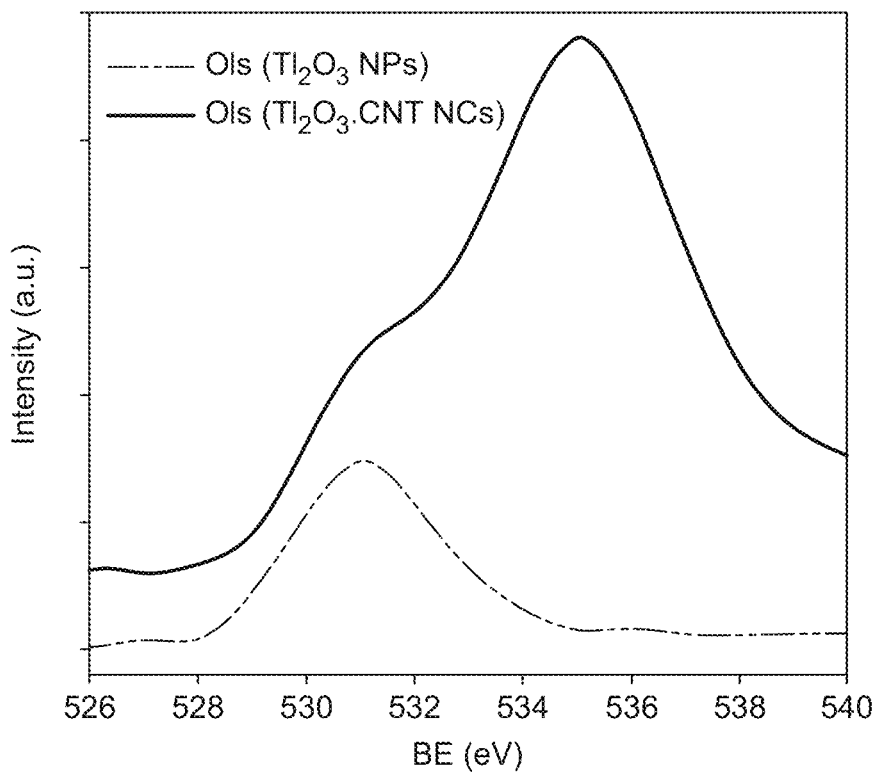
FIG. 5D shows binding energy examination of O1s.

FIG. 5A shows comparative binding energy examination of CNT, $Tl_2O_3$ NPs, $Tl_2O_3$.CNT NCs. The binding energy examination is calculated based on X-ray photoelectron spectroscopy (XPS) used to discover the material environment of the fundamentals found in the prepared $Tl_2O_3$.CNT NCs. Electron number and kinetic energy of a material may be projected throughout XPS examination in which the X-ray may get altered by the presence of nanocomposites. Chemical and electronic nature, fundamental symphony, and the empirical principle of the elements presented in material might be examined by using this process. Based on the XPS examination, carbon, thallium, and oxygen were present in the prepared $Tl_2O_3$.CNT NCs (As shown in FIG. 5A). FIG. 5B, FIG. 5C and FIG. 5D refer to the binding energy examination of $Tl^{3+}$, C1s, and O1s, respectively. Carbon, oxygen, and spin-orbit thallium were assigned in the major peaks at C1s {285.2 (CNT) and 288.8 (NCs)}, O1s {531.0 (NPs) and 535.0 (NCs)}, and $Tl^{3+}$ {118.4, 122.8 (NPs) and 122.6, 126.8 (NCs)} eV in that order indicating that Carbon (C), oxygen ($O^{2-}$), and thallium ($Tl^{3+}$) were present in the prepared $Tl_2O_3$.CNT NCs.

Figure 6:
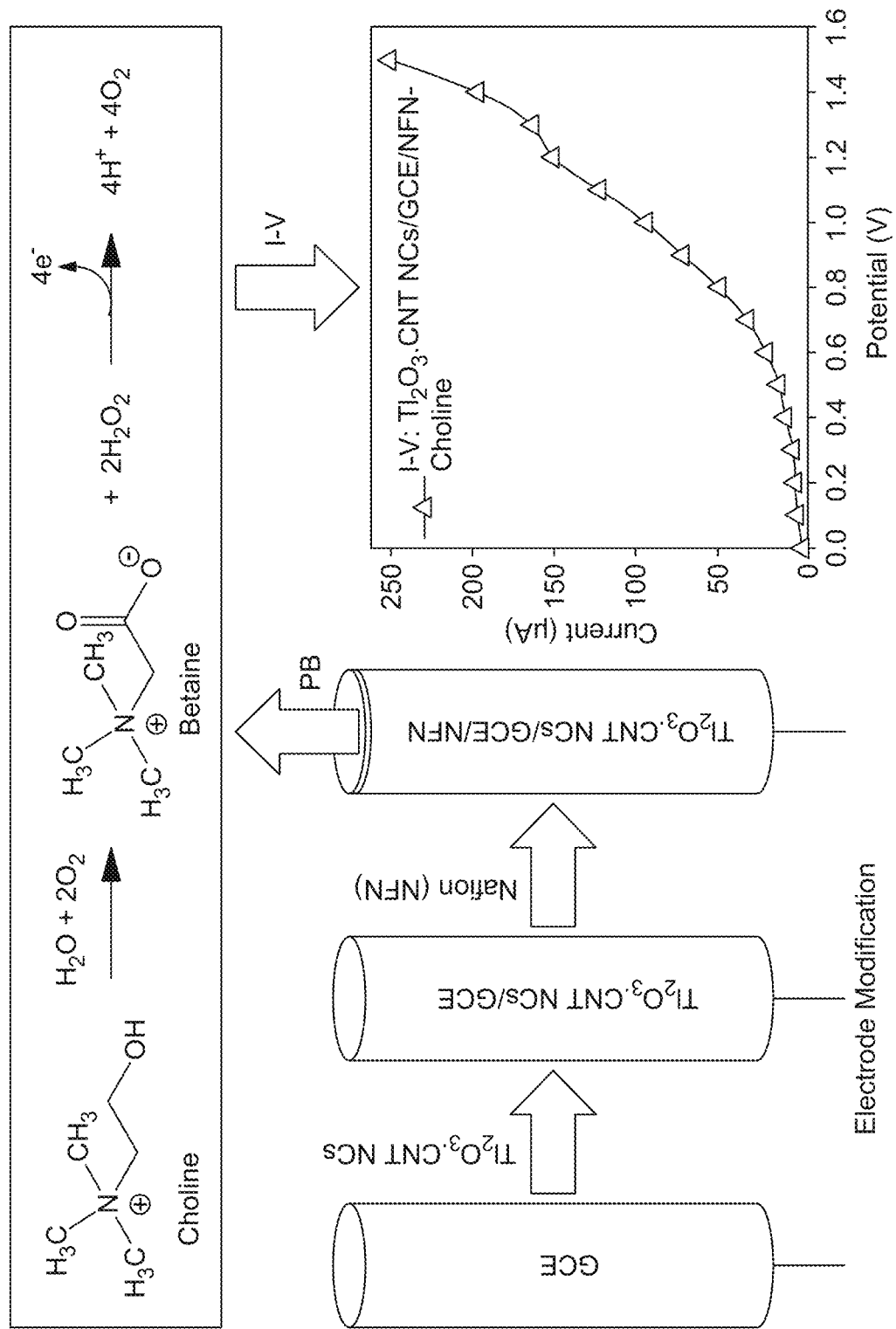
FIG. 6 is a flowchart depicting a method for fabrication of $Tl_2O_3$.CNT NCs on glassy carbon electrode with a polymer matrix (nafion), a proposed electrochemical mechanism of choline at surface modified electrode of the present disclosure, and also depicts outcomes of I-V experimental results.
Figure 7A:
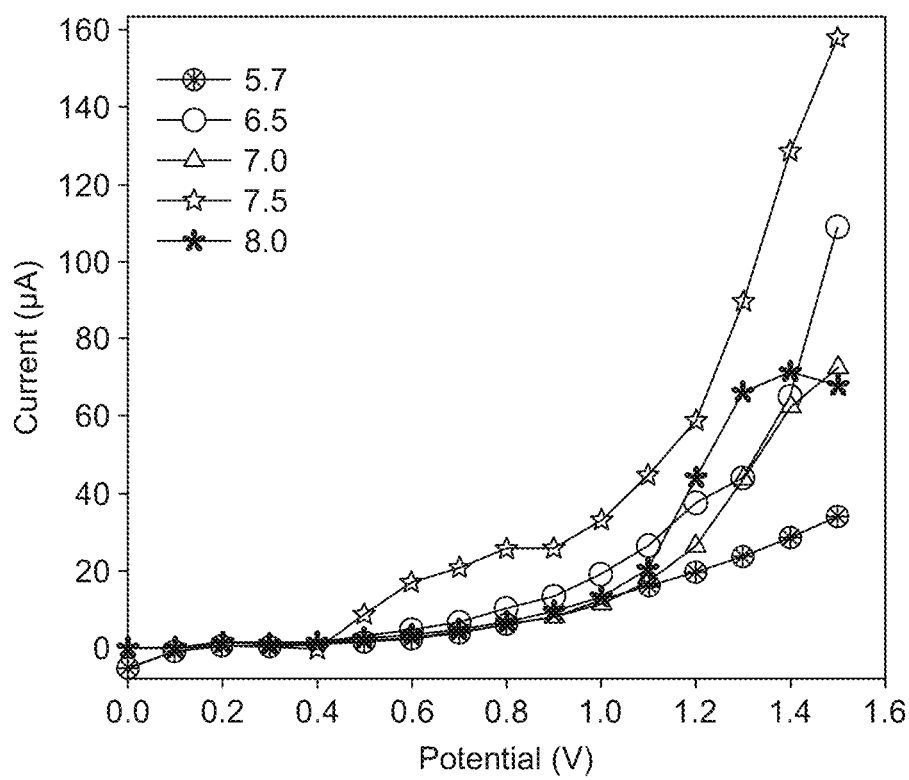
FIG. 7A is a voltammogram depicting the effect of pH on the surface modified electrode in the presence of choline within a pH range of 5.7-8.0.

FIG. 6 is a flowchart depicting a method for fabrication of $Tl_2O_3$.CNT NCs on glassy carbon electrode with a polymer matrix (nafion), a proposed electrochemical mechanism of choline at surface modified electrode of the present disclosure, and also depicts outcomes of I-V experimental results. Development of the biosensor based on modified $Tl_2O_3$.CNT NCs is the preliminary stage in the biological science arena. $Tl_2O_3$.CNT NCs fabricated GCE were experimented with in phosphate buffer for the sensitive identification and detection of the biological molecule, like choline. Electrochemical response of the sensor was dynamically altered due to adsorption of choline during the I-V process. An expected mechanism regarding electrochemical identification and detection of biomolecule based on the two-electrode system is shown in FIG. 6. Choline was converted into betaine and hydrogen peroxide in presence of water and oxygen. Further, hydrogen peroxide was converted into proton and oxygen by releasing four electrons. This change in chemical information (loss of electrons) caused by choline on contact with at least a portion of the working electrode causes the sensor to transduce the change in chemical information associated with choline to an electrical signal. Further, real electrical responses of choline are investigated by simple and reliable I-V technique with electrode of the present disclosure, which is presented in FIG. 6. A significant amplification in the current response with applied potential is noticeably confirmed. Choline in presence of the $Tl_2O_3$.CNT NCs fabricated GCE sensor releases 2 electrons to the reaction system, which improved and enhanced the current responses against potential during the I-V measurement at room conditions.

pH is an important factor affecting the performance of surface modified electrode. The effect of pH of choline on the sensing ability of the surface modified electrode was further evaluated, and the results of this experiment are presented in FIG. 7A. The surface modified electrodes were examined in phosphate buffer arrangement from lower acidic to little basic condition (pH=5.7-8.0). The pH was adjusted using chemicals known in the art. All other process parameters were kept identical while performing the experiment. The current response at different pH was noted. From FIG. 7A, it can be observed that although the electrochemical sensor is effective in detection of choline at a wide range of pH values, best results were observed at a slightly alkaline or neutral pH values. A higher electrical response was recorded at pH=7.5 with the sensor of the present disclosure. From these findings it is evident that the electrode exhibits superior sensitivity with enhanced current response at pH 7.5, because of the higher rate of electron transfer at pH 7.5.

Figure 7B:
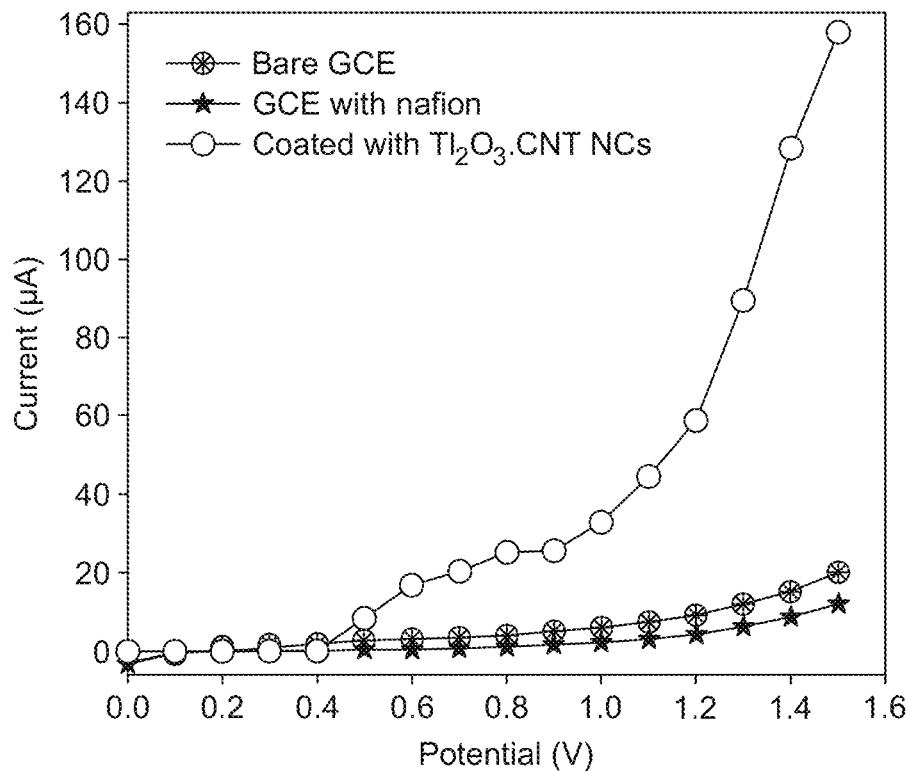
FIG. 7B is a voltammogram comparing the electrochemical behavior with a bare electrode (glassy carbon electrode), glassy carbon electrode with a polymer matrix (nafion) and the surface modified electrode, in sensing choline.

Further, the current response of the surface modified electrode was compared to that of a bare/uncoated electrode (bare GCE), and GCE coated with nafion. The results of this study are presented in FIG. 7B. A difference in the electrical signal is observed for $Tl_2O_3$.CNT NCs covered GCE compared to the bare electrode (GCE and GCE including 5% nafion). The results suggest that the $Tl_2O_3$.CNT NCs.

Figure 7C:
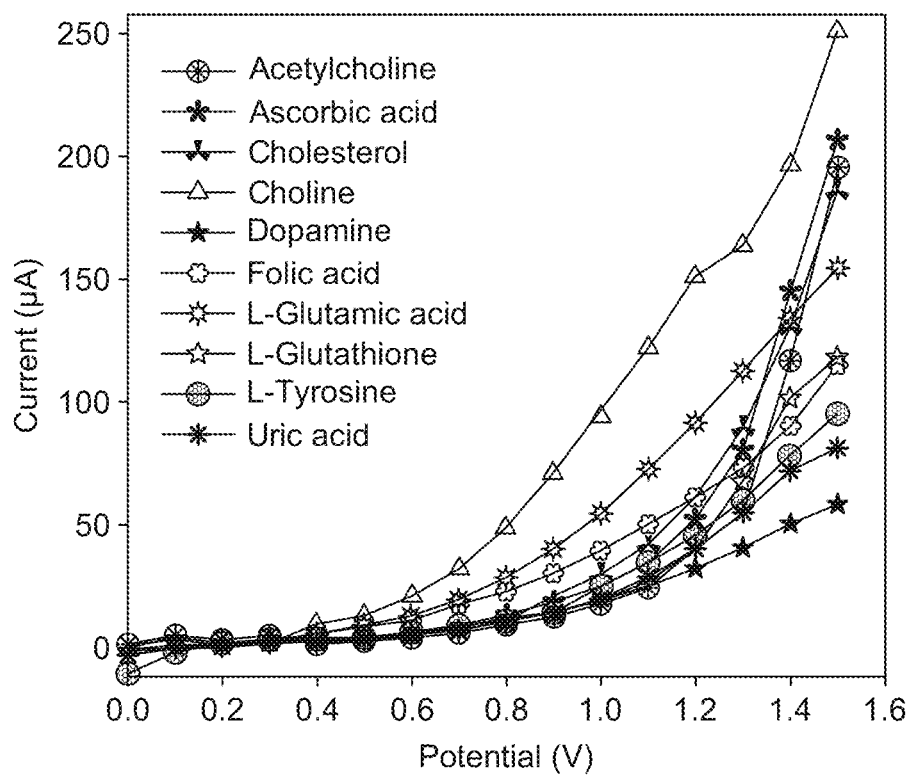
FIG. 7C illustrates a I-V graph depicting the selectivity of the surface modified electrode towards various biomolecules.

One of the most essential and desirable features of an electrochemical sensor lies in its ability to distinguish the analyte of interest, even at very low concentrations, from interfering chemicals. Because of the ability to distinguish interfering agents from choline with very close electrochemical behavior, the interference study is one of the important methods of analytical chemistry. In other words, the electrochemical sensor ought to be selective and sensitive. To assess the selectivity of the electrode towards choline, 25.0 µL of 1.0 µM choline in (10.0 mL, pH=7.5, and 100.0 mM) phosphate buffer was taken. Nine other interfering chemicals, maintained at the same concentration, were added to a sample containing choline. The interfering chemicals are acetylcholine, ascorbic acid, cholesterol, dopamine, folic acid, 1-glutamic acid, 1-glutathione, 1-tyrosine, and uric acid. The results of this study are presented in FIG. 7C. From the FIG. 7C, it can be observed that although the selectivity towards glutamic acid and ascorbic acid was found to be moderate, best amperometric response was observed, given all other reaction conditions kept constant, was observed with choline at applied potential range of 0.1-1.5 V.

Figure 7D:
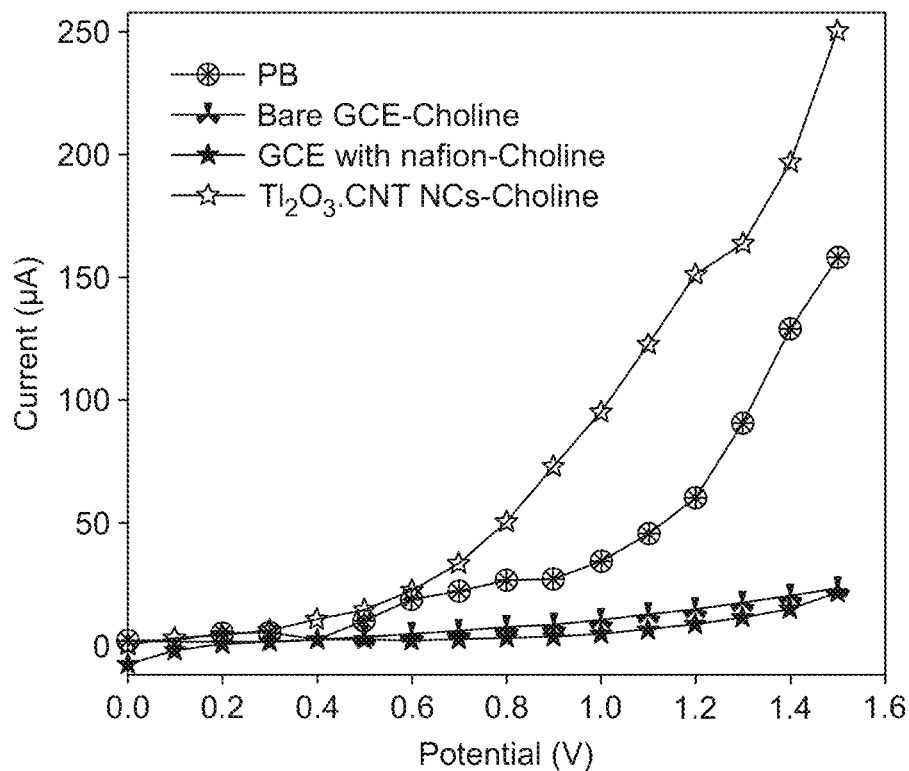
FIG. 7D is a voltammogram comparing the effect of choline on glassy carbon electrode, glassy carbon electrode with a polymer matrix (nafion) and the surface modified electrode.

FIG. 7D shows an electrical response of $Tl_2O_3$.CNT NCs modified electrode in the absence and presence of choline. A control experiment in the absence and presence of choline (concentration=1.0 µM and amount≈25.0 µL) was conducted in the buffer phase (10.0 mL, pH=7.5, and 100.0 mM) to observe the electrical response towards the biomolecule. $Tl_2O_3$.CNT NCs modified electrode showed immense response towards choline compared to other fabricated electrodes such as phosphate buffer (PB), bare GCE, and GCE with nafion.

Figure 8A:
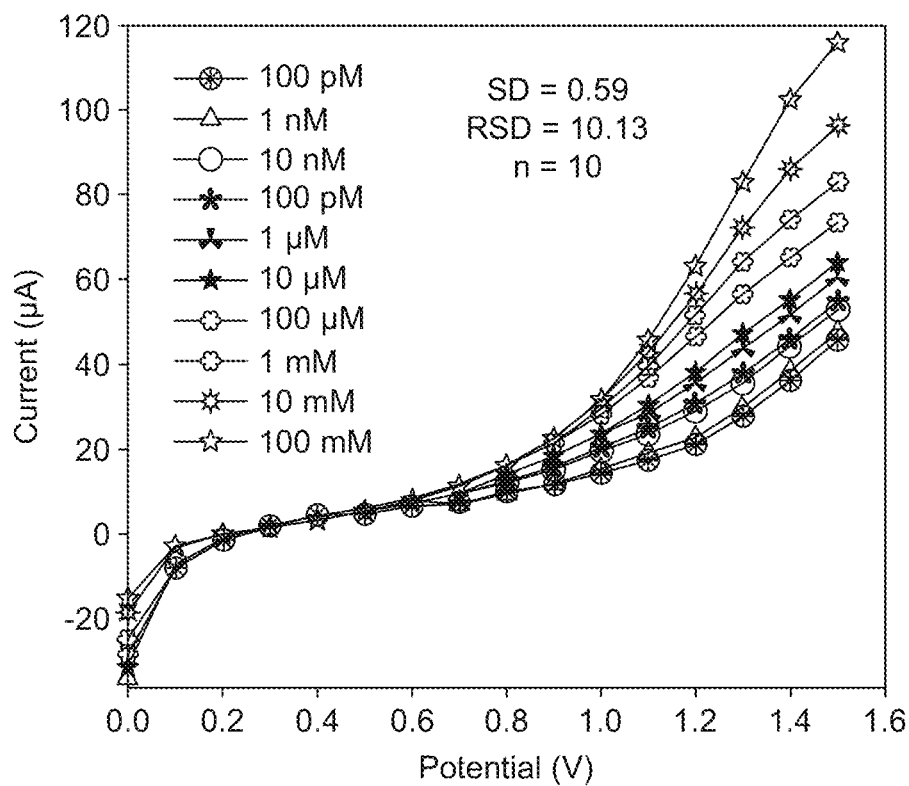
FIG. 8A is an I-V graph depicting the effect of concentration of choline on current change with the surface modified electrode.
Figure 8B:
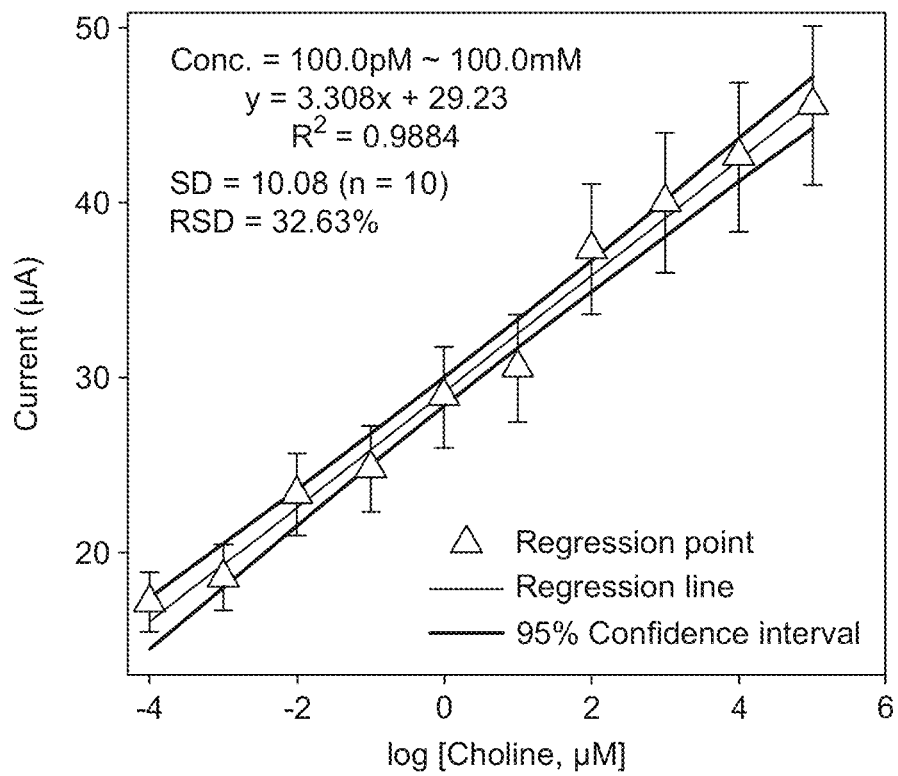
FIG. 8B shows a calibration plot obtained from FIG. 8A vs choline.

FIG. 8A is an I-V graph depicting the effect of concentration of choline on current change with the surface modified electrode. Electrical signals with a concentration range of choline of about 100.0 pM~100.0 mM were tested against the proposed sensor ($Tl_2O_3$.CNT NCs/GCE/NFN) under a customary arrangement to identify the alteration of responses that are used to recognize the biomolecules. It was recorded that electrical responses had been augmented on a usual array from low to high concentration of the choline (SD=0.59, RSD=10.13% at+0.5 V, and n=10). FIG. 8B shows a calibration plot obtained from FIG. 8A vs choline. Calibration bend was plotted at +1.1 V from choline concentration (100.0 µM~100.0 mM), observed linear (R2=0.9884), SD=10.08, RSD=32.63%, n=10, and error bar=10.0%. Analytical parameters of the sensor for example sensitivity (104.68 µAµM-1 $cm^2$), LOD down to 9.14 pM, and LOQ (30.47 µM) were found from calibration bend by means of the equations (x-xii).

$$\text{Sensitivity} = \frac{m}{A} \qquad \text{(x)}$$

$$LOD = \frac{(3 \times SD)}{m} \qquad \text{(xi)}$$

$$LOQ = \frac{(10 \times SD)}{m} \qquad \text{(xii)}$$

Here, m=slope of the calibration bend (y=3.308 x+29.23), A=dynamic surface arena of furnished GCE (perimeter=0.0316 cm$^2$), SD=standard deviation (10.08) of choline concentration in the calibrated impending (+1.1 V) N. M. Rahman, M. M. Hussain, A. M. Asiri., D-Glucose sensor based on ZnO V205 NRs by an enzyme-free electrochemical approach, RSC Adv. 9 (2019) 31670-31682, M. M. Hussain, A. M. Asiri, M. N. Arshad, M. M. Rahman., A Thallium Ion Sensor Development Based on the Synthesized (E)-N'-(Methoxybenzylidene)-4-Methylbenzenesulfonohydrazide Derivatives: Environmental Sample Analysis, Chemistry Select 4 (2019) 10543-10549, M. M. Rahman, M. M. Hussain, A. M. Asiri, K. A. Alamry, M. A. Hasnat., An enzyme free detection of L-Glutamic acid using deposited CuO.GdO nanospikes on a flat glassy carbon electrode, Surfaces Interfaces 20 (2020) 100617].

Figure 8C:
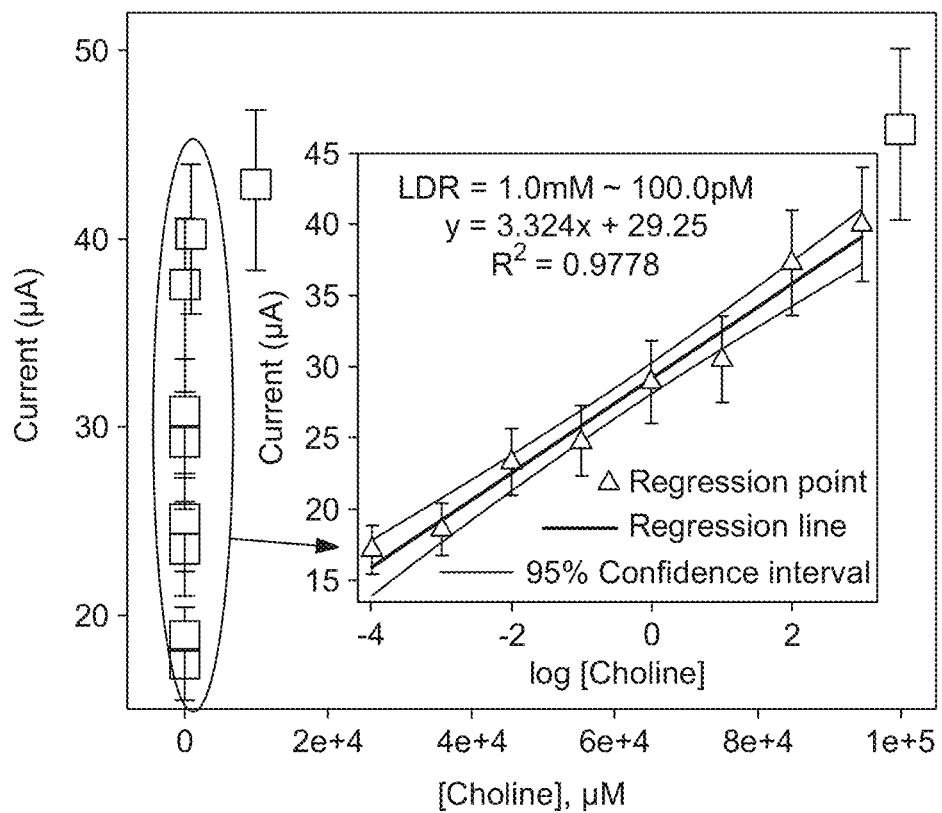
FIG. 8C shows a linear dynamic range plot with an error limit of 10%.
Figure 8D:
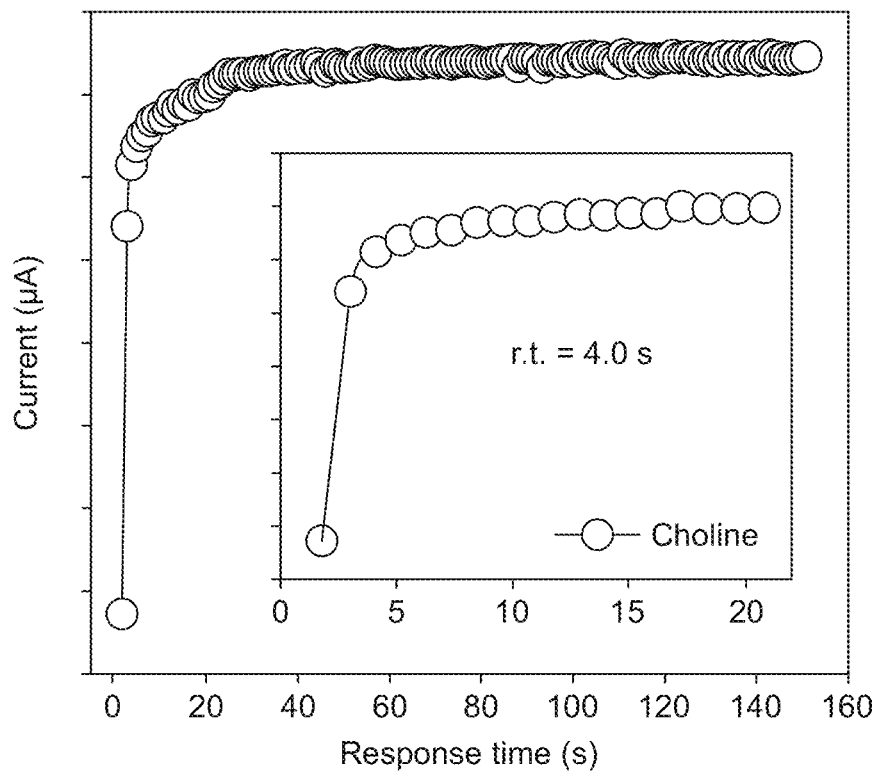
FIG. 8D shows a response time of choline towards the biosensor.

FIG. 8C shows a linear dynamic range graph with an error limit of 10%. Linear dynamic range (LDR=1.0 mM~100.0 pM) is obtained from the calibration bend and observed linear (R2=0.9778) with linear equation, y=3.324 x+29.25. FIG. 8D shows a response time of choline towards the sensor. Response time of choline (concentration=1.0 μM and amount=25.0 μL) towards the sensor (Tl$_2$O$_3$.CNT NCs/GCE/NFN) were examined and determined in buffer phase (10.0 mL, pH=7.5, and 100.0 mM) and in just 4.0 secs.

Figure 9A:
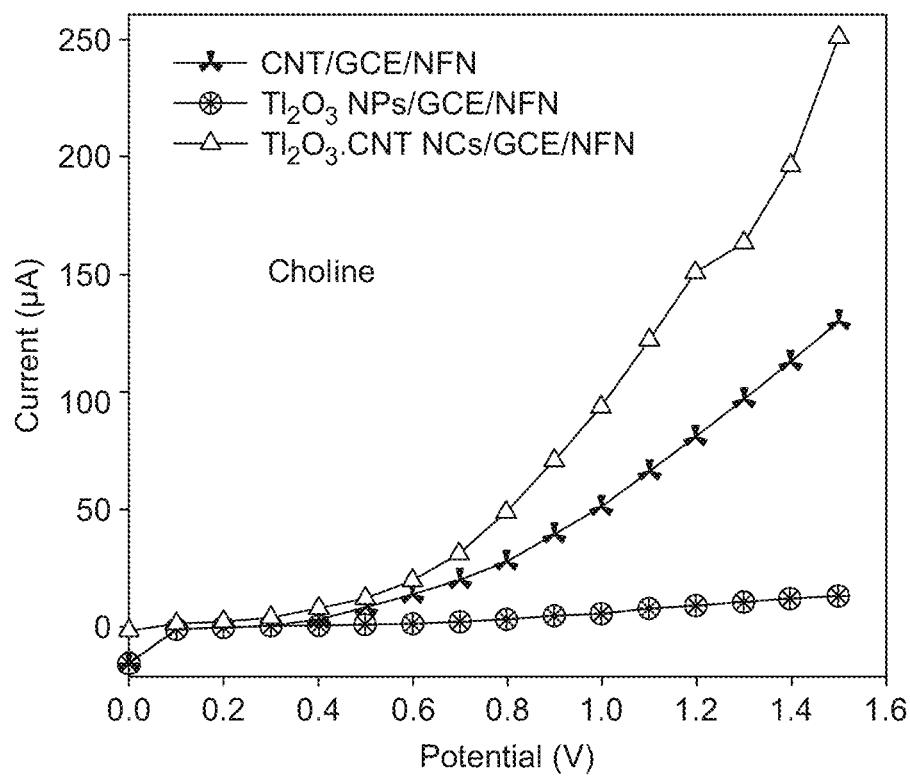
FIG. 9A is a plot comparing the effect of current change with the $Tl_2O_3$.CNT NCs coated electrode sensor with that of bare electrode sensor in responses to choline.
Figure 9B:
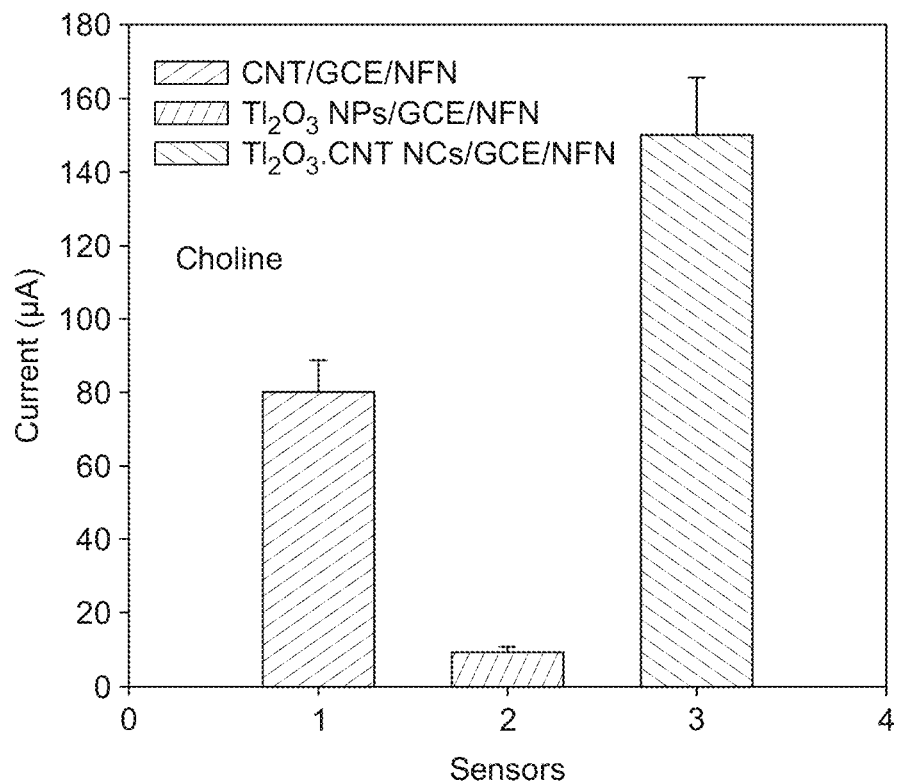
FIG. 9B shows bar diagram depicting the effect of current change with the $Tl_2O_3$.CNT NCs coated electrode sensor with that of bare electrode sensor in response to choline at +1.2 V with error bar 10.0%.

FIG. 9A is a plot comparing the effect of current change with the Tl$_2$O$_3$.CNT NCs coated electrode sensor with that of bare electrode sensor in responses to choline. The sensors used to perform this study are GCE modified with CNTs in presence of nafion; GCE modified with Tl$_2$O$_3$ in presence of nafion; and GCE modified with Tl$_2$O$_3$.CNT in presence of nafion. To understand the electrochemical response of each of these sensors towards choline, 25.0 μL of 1.0 μM choline in buffer phase (10.0 mL, pH=7.5, and 100.0 mM) was taken. It was observed that Tl$_2$O$_3$.CNT NCs/GCE/NFN sensor appeared to have a major electrical response compared to other sensors for example CNT/GCE/NFN and Tl$_2$O$_3$ NPs/GCE/NFN. FIG. 8B shows bar diagram depicting the effect of current change with the Tl$_2$O$_3$.CNT NCs coated electrode sensor with that of bare electrode sensor in response to choline at +1.2 V with error bar 10.0%. A comparison of choline detection with different sensors (prior art) is presented in Table 1.

Figure 10A:
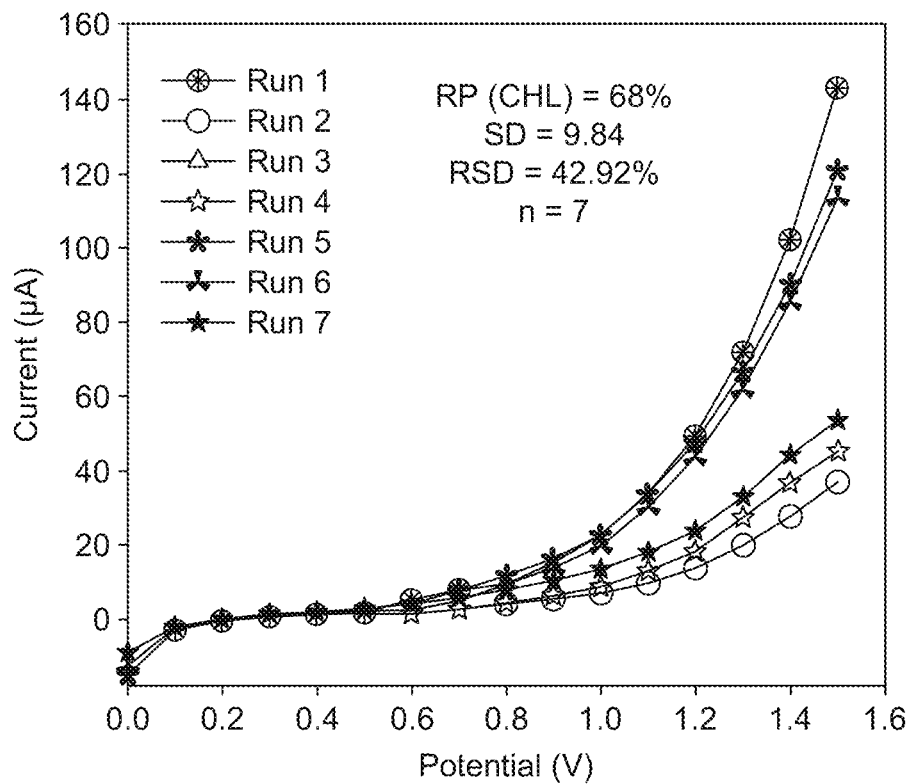
FIG. 10A shows the reproducibility response of $Tl_2O_3$.CNT NCs coated electrode for choline sensing.
Figure 10B:
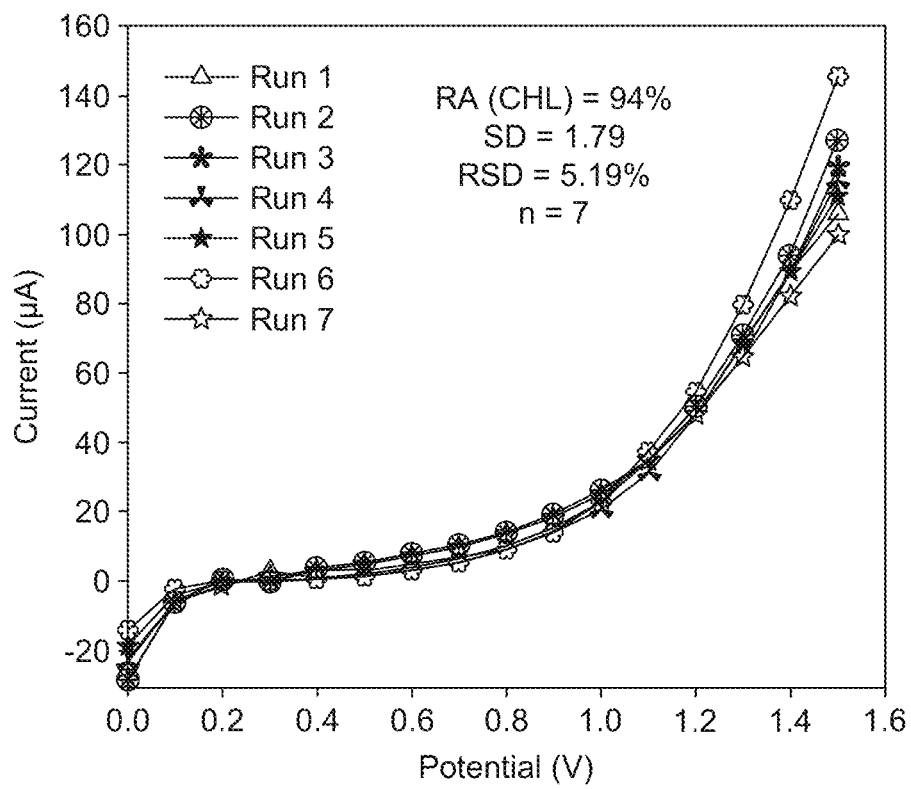
FIG. 10B shows the repeatability response of $Tl_2O_3$.CNT NCs coated electrode for choline sensing.

FIG. 10A and FIG. 10B shows reproducibility and repeatability response of Tl$_2$O$_3$.CNT NCs coated electrode for choline sensing. The effectiveness of the sensor (Tl$_2$O$_3$.CNT NCs/GCE/NFN) was evaluated to find out the methodological efficacy such as reproducibility and repeatability. For this purpose, a progression of seven subsequent measures 25.0 μL of 1.0 μM choline in (10.0 mL, pH=7.5, and 100.0 mM) phosphate buffer was experimented with the sensor of the present disclosure. A good reproducible response was found (RP=68.0%, SD=9.84, RSD=42.92%, and n=7) at the calibrated potential (+1.1 V) (As shown in FIG. 10A). Electrochemical response of the sensor was further analyzed with the intention of expanded storage predisposition. A succession of storage ability of the projected sensor was examined by using similar ornamented electrode with 25.0 μL of 1.0 μM choline in (10.0 mL, pH=7.5, and 100.0 mM) phosphate buffer, and the repeatability was found 94.0% (SD=1.79, RSD=51.9%, and n=7) (as shown in FIG. 10B). It was recorded that the proposed sensor (Tl$_2$O$_3$.CNT NCs/GCE/ NFN) may be used even after several days of analyzing N. M. Hussain, A. M. Asiri, M. M. Rahman, A non-enzymatic electrochemical approach for 1-lactic acid sensor development based on CuO MWCNT nanocomposites modified with a Nafion matrix, New J. Chemistry 44 (2020) 9775-9787, M. M. Hussain, A. M. Asiri, M. M. Rahman, Synthesis, characterization, and physicochemical studies of the synthesized dimethoxy-N'-(phenylsulfonyl)-benzenesulfonohydrazide derivatives and used as a probe for calcium ion capturing: Natural sample analysis, J. Molecular Structure 1214 (2020) 128243, M. M. Rahman, M. M. Hussain, A. M. Asiri., Enzyme-free detection of uric acid using hydrothermally prepared CuO.Fe2O3 nanocrystals, New J. Chem. 44 (2020) 19581-19590].

Figure 11A:
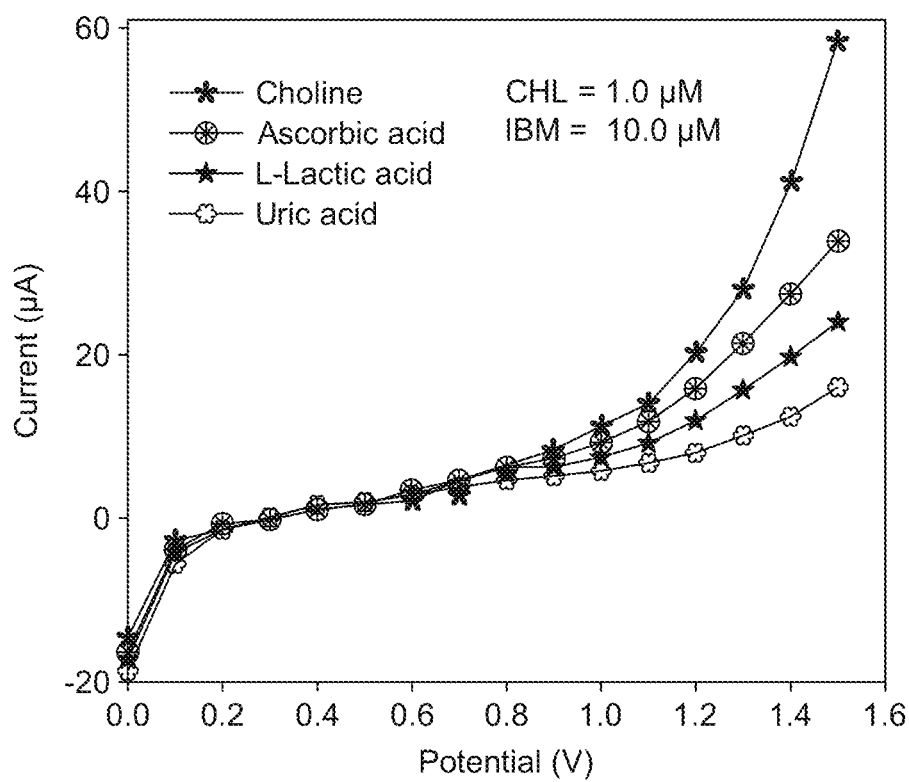
FIG. 11A is a plot depicting interference analysis of the $Tl_2O_3$.CNT NCs coated electrode in the presence of other interfering biomolecules.

FIG. 11A is a plot depicting interference analysis of the Tl$_2$O$_3$.CNT NCs coated electrode in the presence of other interfering biomolecules. Interference examination is a good analytical exercise for recognition of biomolecules having biologically similar characteristics and interfering activity towards the sensor Tl$_2$O$_3$.CNT NCs/GCE/NFN N. M. Rahman, M. M. Hussain, M. N. Arshad, M. R. Awual A. M. Asiri., Arsenic sensor development based on modification with (E)-N0-(2-nitrobenzylidine)-benzenesulfonohydrazide: a real sample analysis, New J. Chem. 43 (2019) 9066-

TABLE 1

Determination of choline using different modified sensors

| Sensors | WP (mV) | Sensitivity (uA mM$^{-1}$ cm$^{-2}$) | LOD (μM) | LDR (μM) | RT (s) | LTS (%) |
| --- | --- | --- | --- | --- | --- | --- |
| AChE-ChO/c-MWCNT ZrO2NPs/GCE | 200 | — | 0.01 | 0.05-200 | 4.0 | 50 |
| ChOx/Silicate/MWCNTs/Pt | 160 | 333.0 | 0.1 | 5-100 | 8 | 91.6, 75.7 |
| ChOx/MnO$_2$/GC | 450 | 24.1 | — | 10-2100 | — | 90, 80 |
| PVA/Au nanorods/ChOx/Pt | 400 | 7.2 | 10 | 20-400 | 20 | 80 |
| PDDA/ChOx/Au/MWCNTs | 350 | 186 | 0.3 | 1-500 | 7 | 82.5 |
| (PDDA/ChOx)$_3$/MnO$_2$/SPE | 480 | 103 | 0.13 | 0.13-100 | 10 | 75 |
| PDDA/ChOx/ZnO/MWCNTs/PG | 400 | 178 | 0.3 | 1-800 | 13 | 94.6 |
| TlO$_3$•CNT NCs/GCE/NFN | 0-1500 | 104.68 (uAuM$^{-1}$ cm$^{-2}$) | 9.14 pM | 1.0~100.0 (mM~pM) | 4.0 | 68, 94 |

WP: working potential, LOD: Limit of detection, LDR: Linear dynamic range, RT: response times, LTS: Long term stability, SPE: Screen-printed carbon electrodes.

9075, A. M. Asiri, M. M. Hussain, M. N. Arshad, M. M. Rahman, A $Ce^{2+}$ sensor based on napthalen-1-ylmethylenebenzenesulfonohydrazide (NMBSH) molecules: ecological sample analysis, New J. Chem. 42 (2018) 4465-4473, A. M. Asiri, M. M. Hussain, M. N. Arshad, M. M. Rahman, Sensitive and selective heavy metal ion, $Mn^{2+}$ sensor development based on the synthesized (E)-N0-chlorobenzylidenebenzenesulfonohydrazide (CBBSH) molecules modified with nafion matrix, J. Indust. Engr. Chem. 63 (2018) 312-321, M. M. Hussain, A. M. Asiri, M. M. Rahman, Hg2+ Sensor Development Based on (E)-N'-NitrobenzylideneBenzenesulfonohydrazide (NBBSH) Derivatives Fabricated on a Glassy Carbon Electrode with a Nafion Matrix, ACS Omega 2 (2017) 420-431]. Ascorbic acid, L-lactic acid, and uric acid were used as interfering biomolecules to determine the electrochemical responses towards the sensor for choline detection. For this purpose, a fluid sample containing 25.0 µL of 1.0 µM choline in buffer phase (10.0 mL, pH=7.5, and 100.0 mM) was taken and 25.0 µL of 10.0 µM of other interfering biomolecules (ascorbic acid, L-lactic acid, and uric acid) were added to determine the selectivity of the sensor towards choline. The actions of interfering biomolecules and choline towards the anticipated sensor were calculated in the calibrated potential (+1.1 V); it was observed that despite the interfering biomolecules having a concentration 10-fold greater that the concentration of choline, the selectivity of the sensor towards choline was considered to be 100.0%.

Figure 12:
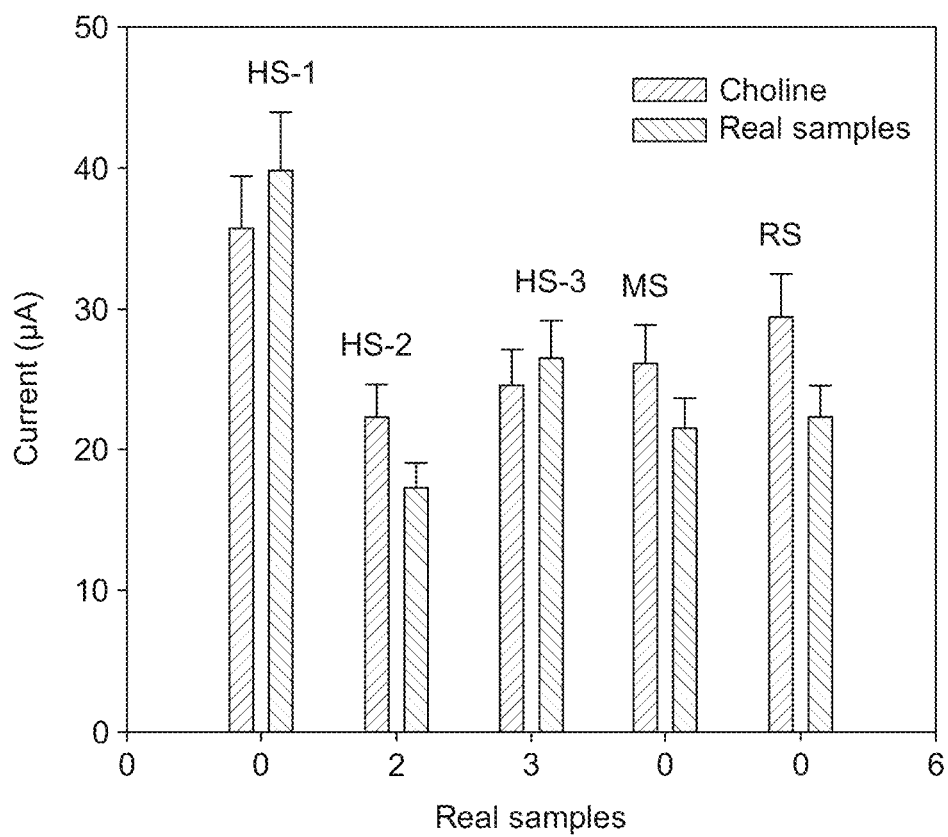
FIG. 12 is an I-V graph determining choline concentration from various biological samples with the sensor of the present disclosure

FIG. 12 is an I-V graph determining choline concentration from various biological samples with the sensor of the present disclosure. For this purpose, detailed experimentation was accomplished in order to analyze biological samples for example human serum (HS), mouse serum (MS), and rabbit serum (RS) with $Tl_2O_3$.CNT/GCE/NFN sensor for identification of choline concentration on the basis of a standard addition technique [M. M. Rahman, M. M. Hussain, M. N. Arshad, A. M. Asiri., The synthesis and application of (E)-N'-(benzo[d]dioxol-5-ylmethylene)-4-methyl-benzenesulfonohydrazide for the detection of carcinogenic lead, RSC Adv. 10 (2020) 5316-5327, M. M. Hussain, A. M. Asiri, M. N. Arshad, M. M. Rahman, A Thallium Ion Sensor Development Based on the Synthesized (E)-N'-(Methoxybenzylidene)-4-Methylbenzenesulfonohydrazide Derivatives: Environmental Sample Analysis, ChemistrySelect 4 (2019) 10543-10549, M. M. Hussain, A. M. Asiri, M. N. Arshad, M. M. Rahman, Fabrication of a Ga3+ sensor probe based on methoxybenzylidenebenzenesulfonohydrazide (MBBSH) by an electrochemical approach, New J. Chem. 42 (2018) 1169-1180, M. M. Hussain, A. M. Asiri, M. N. Arshad, M. M. Rahman, Development of selective Co2+ ionic sensor based on various derivatives of benzenesulfonohydrazide (BSH) compound: An electrochemical approach, Chem. Engr. J. 339

TABLE 2

Examination of interference effect towards the sensor ($TlO_3$•CNT NCs/GCE/NFN)

| | Observed current (µA) | | | | | | IF | SD | RSD % |
|---|---|---|---|---|---|---|---|---|---|
| IBM | R1 | R2 | R3 | R4 | R5 | Average | (%) | (n = 3) | (n = 30) |
| CHL | 16.76 | 18.31 | 16.74 | 3.53 | 14.28 | 13.92 | 100 | 5.99 | 43.00 |
| AA | 14.48 | 11.52 | 12.88 | 10.60 | 10.13 | 11.92 | 86 | 1.77 | 14.88 |
| L-LA | 11.63 | 9.42 | 8.67 | 8.50 | 8.15 | 9.27 | 67 | 1.40 | 15.06 |
| UA | 7.62 | 6.89 | 6.60 | 6.45 | 6.24 | 6.76 | 49 | 0.54 | 7.93 |

IBM: Interfering biomolecules, R: Reading, IE: Interfering effects, SD: Standard deviation, and RSD: Relative standard deviation.

Figure 11B:
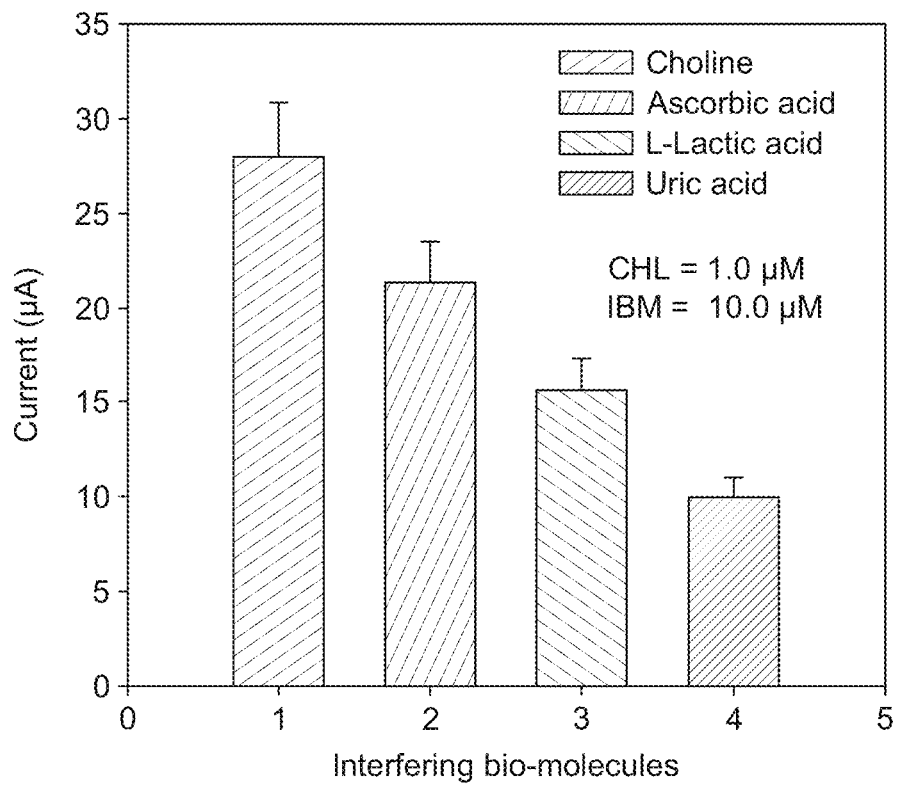
FIG. 11B shows a bar diagram depicting current change response to the interfering biomolecules at +1.3 V with an error limit of 10.0%.

It was found that $Tl_2O_3$.CNT NCs/GCE/NFN sensor did not show any significant electrochemical response towards the interfering biomolecules having ten times more concentration than choline. The sensor may be a good investigative appliance to detect sensitive biological molecules with good selectivity. FIG. 11B shows a bar diagram depicting current change response to the interfering biomolecules at +1.3 V with an error limit of 10.0%.

(2018) 133-143]. A set amount (~25.0 µL) of each biological sample was examined in phosphate buffer (amount=10.0 mL, pH=7.5, and concentration=100.0 mM) and respective calculation was performed at the calibrated potential (+1.1 V) to detect choline concentration in HS, MS, and RS. The results establish that current-voltage procedure might be a good experimentation tool for the analysis of biomolecules in biological sciences area.

TABLE 3

Biological sample analysis

| OE | AC, CHL (25 µL, µM) | OC, CHL (µA) | BSA (25 µL) | ROC (BAS, µA) | | | | FC (µM) | R (%) | SD (n = 3) | RSD (%) n = 3 |
|---|---|---|---|---|---|---|---|---|---|---|---|
| | | | | R1 | R2 | R3 | A | | | | |
| 1 | 1.0 | 35.79 | HS-1 | 41.98 | 38.89 | 38.70 | 39.86 | 1.11 | 111 | 1.84 | 4.62 |
| 2 | 1.0 | 22.35 | HS-2 | 19.61 | 16.71 | 15.82 | 17.38 | 0.78 | 78 | 1.98 | 11.40 |
| 3 | 1.0 | 24.59 | HS-3 | 26.08 | 27.52 | 25.85 | 26.48 | 1.08 | 108 | 0.91 | 3.42 |
| 4 | 1.0 | 26.17 | MS | 24.18 | 21.19 | 19.24 | 21.54 | 0.82 | 82 | 2.49 | 11.55 |
| 5 | 1.0 | 29.51 | RS | 21.49 | 21.10 | 24.26 | 22.28 | 0.76 | 74 | 1.72 | 7.73 |

OE: Ornamented electrode, AC: Added concentration, CHL: Choline, OC: Observed current, RSA: Real sample added, ROC: Respective observed current, BSA: Biological sample added, R: Reading, A: Average, FC: Found concentration, RC: Recovery, SD: Standard deviation, RSD: Relative standard deviation, HS: Human serum, MS: Mouse serum, and RS: Rabbit serum.

INDUSTRIAL APPLICABILITY

The biosensor of the present disclosure offers several advantages over the prior art for detection of choline. One advantage of the embodiments according to the present disclosure is that the biosensor using thallium oxide-based nanomaterial electrode shows good reliability, reproducibility, and stability under ambient conditions. The $Tl_2O_3$.CNT NCs coated electrode shows a better electrical response than the uncoated GEC. Another advantage of the biosensor is that it a non-enzymatic electrochemical method for the detection of biomolecules. Yet another advantage of the embodiments of the present disclosure is the good detectability, high sensitivity, and high selectivity for choline compounds which is important for the diagnosis of major diseases. Enhanced electro-catalytic property in detecting choline, handy nature, good reproducibility, wide LDR, high sensitivity, and low LOD, makes this biosensor an excellent choice for the detection of choline.

It is understood that the examples, embodiments and teachings presented in this application are described merely for illustrative purposes. Any variations or modifications thereof are to be included within the scope of the present application as discussed.

ACKNOWLEDGMENT

The authors extend their appreciation to the Deputyship for Research & Innovation, Ministry of Education in Saudi Arabia for funding this research work through the project number "2021-042" and King Abdulaziz University, DSR, Jeddah, Saudi Arabia.

The invention claimed is:

1. A biosensor for detecting a biological molecule comprising a surface modified electrode comprising:
   - a glassy carbon electrode (GCE);
   - a nanomaterial disposed on the glassy carbon electrode, wherein the nanomaterial comprises carbon nanotubes (CNTs), and at least one of thallium oxide nanoparticles ($Tl_2O_3$ NPs), thallium oxide ($Tl_2O_3$) nanopowder and thallium oxide carbon nanotube nanocomposites ($Tl_2O_3$ CNT NCs); and
   - a polymer matrix configured to bind the glassy carbon electrode with the nanomaterial.

2. The biosensor according to claim 1, wherein the biological molecule is one selected from a group consisting of acetylcholine, ascorbic acid, cholesterol, choline, dopamine, folic acid, L-glutamic acid, L-glutathione, L-tyrosine, and uric acid.

3. The biosensor according to claim 1, wherein the biological molecule is choline.

4. The biosensor according to claim 3, configured to detect choline across a concentration range of 100.0 pM~100.0 mM.

5. The biosensor according to claim 3, having a sensitivity of 104.68 $\mu A \mu M^{-1} cm^{-2}$.

6. The biosensor according to claim 3, wherein the biosensor has a linear dynamic range of 100.0 pM-1.0 mM.

* * * * *